US010301631B2

(12) United States Patent
Franciskovich et al.

(10) Patent No.: US 10,301,631 B2
(45) Date of Patent: *May 28, 2019

(54) BIOLOGICAL INDICATOR

(71) Applicant: American Sterilizer Company, Mentor, OH (US)

(72) Inventors: Phillip P. Franciskovich, Concord, OH (US); Tricia A. Cregger, Fairlawn, OH (US); William A. Yirava, Willoughby, OH (US); Peter A. Burke, Concord, OH (US)

(73) Assignee: American Sterilizer Company, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/001,203

(22) Filed: Jun. 6, 2018

(65) Prior Publication Data

US 2018/0273957 A1 Sep. 27, 2018

Related U.S. Application Data

(63) Continuation of application No. 15/618,158, filed on Jun. 9, 2017, now Pat. No. 10,017,772, which is a continuation of application No. 15/204,079, filed on Jul. 7, 2016, now Pat. No. 9,695,428, which is a continuation of application No. 14/512,708, filed on Oct. 13, 2014, now Pat. No. 9,416,393.

(51) Int. Cl.
| | |
|---|---|
| *C12Q 1/22* | (2006.01) |
| *C12Q 1/34* | (2006.01) |
| *C12Q 1/68* | (2018.01) |
| *C12N 15/75* | (2006.01) |
| *A61L 2/28* | (2006.01) |
| *C12M 1/34* | (2006.01) |
| *C12Q 1/689* | (2018.01) |
| *C12M 1/12* | (2006.01) |
| *C12Q 1/6897* | (2018.01) |
| *C12N 9/38* | (2006.01) |

(52) U.S. Cl.
CPC ............... *C12N 15/75* (2013.01); *A61L 2/28* (2013.01); *C12M 1/34* (2013.01); *C12M 37/06* (2013.01); *C12N 9/2471* (2013.01); *C12Q 1/22* (2013.01); *C12Q 1/34* (2013.01); *C12Q 1/689* (2013.01); *C12Q 1/6897* (2013.01); *C12Y 302/01023* (2013.01)

(58) Field of Classification Search
CPC . C12Q 1/22; C12Q 1/34; C12Q 1/689; C12Q 1/6897; A61L 2/28; C12N 9/2471; C12N 15/75; C12Y 302/01023; C12M 1/34
See application file for complete search history.

(56) References Cited

U.S. PATENT DOCUMENTS

| | | | |
|---|---|---|---|
| 8,372,624 B2 | 2/2013 | Franciskovich et al. | |
| 8,507,248 B2 | 8/2013 | Franciskovich et al. | |
| 8,945,837 B2 | 2/2015 | Franciskovich et al. | |
| 9,416,393 B2 * | 8/2016 | Franciskovich | ....... C12M 37/06 |
| 9,695,428 B2 * | 7/2017 | Franciskovich | ....... C12M 37/06 |
| 9,701,968 B2 * | 7/2017 | Franciskovich | ....... C12M 37/06 |
| 10,011,843 B2 * | 7/2018 | Franciskovich | ....... C12M 37/06 |
| 10,011,844 B2 * | 7/2018 | Franciskovich | ....... C12M 37/06 |
| 10,017,772 B2 * | 7/2018 | Franciskovich | ....... C12M 37/06 |
| 2013/0217107 A1 | 8/2013 | Pederson et al. | |
| 2013/0224849 A1 | 8/2013 | Chandrapati et al. | |

FOREIGN PATENT DOCUMENTS

| | | |
|---|---|---|
| WO | 0214490 | 2/2002 |
| WO | 2008079469 | 7/2008 |

OTHER PUBLICATIONS

Mahillon et al.; Microbiology and Molecular Biology Reviews, Sep. 1998, p. 725-774; vol. 62, No. 3.
Novotny et al.; "S-layer glycan-specific loci on the chromosome of Geobacillus stearothermophilus NRS 2004/3a and dTDP-L-rhamnose biosynthesis potential of G. stearothermophilus strains"; Microbiology, Apr. 2004, vol. 150, No. 4, pp. 953-965.
Xu et al.; "On Two Transposable Elements from Bacillus stearothermophilus"; PLASMID 29, 1-9 (1993).
Kreuzer et al.; "Identification and Sequence Analysis of the Bacillus subtilis W23 xylR Gene and xyl Operator"; Journal of Bacteriology, Jul. 1989, p. 3840-3845.
International Search Report and Written Opinion for corresponding international application PCT/US2015/035936 dated Oct. 1, 2015.
Siguier et al.; "Insertion sequences in prokaryotic genomes"; Current Opinion in Microbiology; 2006; pp. 526-531.
Albert et al.; "Biological indicators for steam sterilization: characterization of a rapid biological indicator utilizing Bacillus stearothermophilus spore-associated alpha-glucosidase enzyme"; Journal of Applied Microbiology; 1998; pp. 865-874.
De Palmenaer et al.; "IS4 family goes genomic"; BMC Evolutionary Biology; 2008.

* cited by examiner

*Primary Examiner* — Padmavathi Baskar
(74) *Attorney, Agent, or Firm* — Renner, Otto, Boisselle & Sklar, LLP

(57) ABSTRACT

This invention relates to a biological indicator derived from a composition comprising: a host organism comprising a spore forming bacteria; a reporter gene for producing an indicator enzyme; a regulatory gene; and a vehicle for inserting the reporter gene and the regulatory gene in the host organism; the host organism bearing a transposable genetic element in its genome for inserting an insertion sequence in the regulatory gene; the insertion sequence comprising a transposase, a pair of terminal inverted repeat sequences, and at least one open reading frame for expressing the transposase. The vehicle may be taken up by the host organism. The insertion sequence may be inserted in the regulatory gene. The host organism may undergo sporulation to form the biological indicator. A process and an apparatus for using the biological indicator are disclosed.

22 Claims, 9 Drawing Sheets

Specification includes a Sequence Listing.

```
IS10R    CTGATGAATCCCCTAATGATTTTGGTAAA
         CTGAGAGATCCCCTCATAATTTCCCCAAA
IS8402   CTTAACGGGTGACAAGGCATCTCTAGCCT
         CTTAACGGGTGACAACGTAGCTACGAAGC
IS4Sa    TAAGAGAGTTAATTTATAATCTATTTTCA
         TAAGGATGTTAATTTATTAATTTAAAAGG
IS5377   CAGGCGTGTTGATTATCCAATAAAATCCA
         CACGAGTGTTGATTATCCAAAATTATACA
IS231A   CATGCCCATCAACTTAAGAATCTAGACTA
         CATGCCCATCAACTTAAGAACAAAAATAA
IS231V   CATCGCCATCAAGCTAAGGAAAAGGAGAT
         CATCGCCATCAAGCTAACGAAATTGAACT
IS186B   CATAAGCGCTAACTTAAGGGTTGTGGTAT
         CATAAGCGCTAACTTAAGGGTTGAACCAT
IS4      TAATGCCGATCAGTTAAGGATCAGTTGAC
         TAATGCCAGTCAGTTAAGCAACTGACTGG
IS50R    CTGACTCTTATACACAAGTAGCGTCCTGA
         CTGTCTCTTGATCAGATCTTGATCCCCTG
IS1452   CACTACAGTTGCATTTTGTGTTGAGTTCT
         CACTACAGTTGCATTTTGTGTCGTGAGTG
ISH27-1  CAGTACCTCACAAAGCCGGTTAGTTGAGA
         CAGTACCTCACAAAGCATTCTCGGCTAGC
IS1151   CATGGCCGTCAACCTAAGAAGCCTTATTT
         CATGGCCGTCAACCTAAGAAGGCATAAAA
IS942    CCTTAATTCCGCAACACTATAGTTTAACA
         CCTCAAATCCGCAACCTATAGGGTTTAGT
```

FIG. 1B

*IS21*        NONE

*IS53*
L1: GCTGACCGAAAACTGACCCAG    (9-28)
L2: GCCGACTGAAAACTGACCCAG    (42-62)
R1: GCTGATTGAAAACTGACCCAC    (2528-2548) CS
R2: GCCGATTGAAAATTGACCCAG    (2504-2524) CS

*IS232A*
L1: TAAATATGTACATTAACGCTTG         (16-37)
L2: TAAATATGTACATTTTCAATTGGATTCT   (40-67)
L3: TTAGTATGTATATTAAGCTAGATATTCA   (88-115)
R1: TAAACATGTACATTTTCGCTTG         (2148-2169) CS
R2: TAAGCATGTACAAAATCAATCATTTTCT   (2118-2145) CS

*IS408*
L1: TTCCGGCGAACGTGATCACGCAT   (7-29)
L2: TTCGGCGGATCGTGATCATGGAT   (30-52)
L3: TTCGGTTGATCGTGATCGCTGAT   (76-98)
R1: TTTCGGTGATGGTGATCAGGCGT   (7-29) CS
R2: TTCGGCGAACGTGATCAGTTTG    (30-51) CS

*IS5376*
L1: TAAAGCCGATGATAAAATCCCCA   (4-26)
L2: TATAGCCGGAATAAAATTCCCCA   (28-52)
R1: CAAGGCCGATTATTTTTTCCCCA   (2082-2104) CS
R2: AATCGCCGGTTTAAAATTCCCCA   (2058-2080) CS

*IS1162*
L1: CGTGACCGGCTGTTTCG      (18-34)
L2: CGTGACCGGACATTTCG      (41-57)
L3: CGTGACCGCTCATTTCG      (64-80)
L4: CGTGACCG---ATTTC       (88-100)
L5: CGTGACCGCCTGTTTCG      (111-127) CS
L6: CGTGACCGACGATTTCG      (134-150) CS
R1: CGTGACCGCTCATTTCG      (2602-2618) CS
R2: CGTGACCGGTGGCTTCA      (2578-2594) CS

*IS1326*
L1: GAGTTGCATCTAAAATTGACCC    (5-26)
L2: GATTTGCGTCGAAATTTGACCC    (39-60)
L3: GATATTGAGCGCAATTCGACGC    (122-143)
R1: GATTTGCATTGAATTTTGACCC    (2421-2442) CS
R2: GATTTGCACCCAAATTTGACCC    (2445-2466) CS

*IS1415*
L1: GTAAGCTCCCCACTGGCGGCCA    (15-36)
L2: GGTTTCTCCCCGCGTACGGCCA    (60-81)
R1: AAGTTCTCCCCGTAGGCGGCCA    (2545-2566) CS
R2: -AGTTCTCCCCGCTGGTGGCCA    (2521-2542) CS
R3: G-GTTCTCCCCGGTGGCGGCCA    (2498-2519) CS

FIG. 2C

BIOLOGICAL INDICATOR

This application is a continuation of U.S. patent application Ser. No. 15/618,158, filed Jun. 9, 2017, which was a continuation of U.S. patent application Ser. No. 15/204,079, filed Jul. 7, 2016, which was a continuation of U.S. patent application Ser. No. 14/512,708, filed on Oct. 13, 2014. These prior applications are incorporated herein by reference.

TECHNICAL FIELD

This invention relates to biological indicators. These biological indicators may be used for determining the effectiveness of sterilization processes.

BACKGROUND

In the health care industry as well as in many other commercial and industrial applications, it is often necessary to monitor the effectiveness of processes used to sterilize equipment such as medical and non-medical devices, instruments and other articles and materials. Sterilization monitors can be included in the batch of articles to be sterilized to assay the lethality of the sterilization process. They can also be used to validate the effectiveness of sterilization equipment and sterilization cycles used in such equipment.

SUMMARY

Classical methods of sterility assurance typically involve exposing a sterilization indicator containing one or more test organisms to the sterilization process and then measuring the outgrowth of any surviving test organisms. Sterility may be assured if there is no outgrowth of the test organisms following exposure to the sterilization process. Bacterial spores are typically used as the test organisms. Upon completion of the sterilization process, the sterilization indicator is exposed to a liquid growth support medium under conditions that would promote the growth of any surviving test organism cells. The growth support medium often contains a chemical dye which changes color in response to actively growing (metabolizing) cells. Because of the requirement for growth and metabolism, the processes employing these test organisms typically require about 24 to 72 hours of incubation before the effectiveness of the sterilization process can be determined.

A problem with this process relates to the fact that many users of sterilized articles, such as health care facilities and the like, have limited resources and may reuse the "sterilized" articles within 24 to 72 hours and sometimes immediately. In such settings, the 24 to 72 hour holding period for sterility verification may be impractical, costly and inefficient.

A detection process for reading out test results more rapidly for certain 121° C. and 132° C. gravity and pre-vacuum steam sterilization cycles and ethylene oxide sterilization cycles has been proposed. The time necessary to observe evidence of surviving indicator cells is reported to be as little as one hour. This process involves detecting the catalytic activity of the enzyme alpha glucosidase.

This enzyme is produced by a microorganism as a normal component of its metabolism and may be present in the spore coat of the microorganism both before and during sterilization. The presence of this enzyme can be detected by reading fluorescence produced by the breakdown of a non-fluorescent enzyme substrate. Breakdown of the enzyme substrate can be an early detection alternative to waiting for a visual pH color change to indicate a failed sterilization process. Neither growth nor metabolism is required for the fluorometric signal. This results in a reduction in the time required to observe a failure in the sterilization process. However, the enzyme alpha glucosidase is thermophilic in origin, and may be more resistant to heat than the microorganism from which it is derived. This can lead to nuisance failures, a circumstance in which the test microorganism has been, in fact, killed but the indicator enzyme indicates that the test microorganism remains viable. In addition, since the enzyme alpha glucosidase may be present in the spore coat of the test microorganism and its presence does not necessitate metabolism, the detection of this enzyme may not be a direct indication of life.

There are situations where the use of enzyme alpha glucosidase may fail to discriminate an unsuccessfully sterilized load. Successful steam sterilization is dependent upon achieving an effective temperature and pressure for a minimum length of time. Bacterial spores are typically selected as the test organism for this process because they are highly resistant to this combination of parameters. It takes a particularly lethal combination of temperature, pressure and time to kill bacterial spores. Although the target/reporter molecule (alpha glucosidase) is a catalytic enzyme associated with a thermophilic organism, and thus somewhat resistant to heat, it is the heat of the process which ultimately destroys the function of the enzyme. That is, pressure and time play a reduced role in the denaturation of alpha glucosidase. Therefore, under sub-lethal pressure or time conditions the indicator enzyme may be destroyed even though the bacterial spores may not be destroyed. This can result in a failure to detect a non-sterilized load.

The inability of existing technology to account for all the parameters relating to cell death means that "grow out" may be required to provide the final confirmatory result. However, a major drawback with processes requiring what is traditionally known as grow out relates to the time delay in obtaining results for the sterilization test. Sterilization indicators requiring grow out normally employ the use of bacterial spores which must be cultured for at least about 24 to 72 hours to assure adequate detection of any surviving spores. During this time, the articles that went through the sterilization process and are under evaluation should not be used until the results of the spore viability test have been determined. However, as indicated above, this may be impractical for many users of articles requiring sterilization.

U.S. Pat. No. 8,372,624 discloses a process for detecting the effectiveness of a sterilization process wherein a genetically engineered biological indicator is exposed to the sterilization process. The biological indicator comprises a test organism, a reporter gene for producing an indicator enzyme, and a repressor gene that inhibits expression of the reporter gene until the reporter gene is exposed to an inducer (e.g., xylose). The biological indicator may be used in a device that includes two compartments, one compartment for containing the biological indicator, and the other compartment for containing a growth medium that includes the inducer and an enzyme substrate. Once the sterilization is complete, the biological indicator is combined with the growth medium, and any cells from the biological indicator that have survived the sterilization process are incubated. The living cells from the biological indicator are detected when the indicator enzyme acts upon the enzyme substrate to form a product that can be detected. A problem that often occurs with this process involves discoloration due to degradation of the inducer. The inducer is degraded by heating or by exposure to various sterilization mediums (e.g., vaporous hydrogen peroxide, ethylene oxide, etc.), and as a result turns brown or is otherwise discolored. This browning or discoloration can interfere with detecting changes associated with the success or failure of the sterilization, and thereby reduces the sensitivity of the test.

Thus, a problem that has been presented by the art is to provide a biological indicator that accurately detects the effectiveness of a sterilization process within a relatively short period of time, and in doing so, does not rely on the use of an inducer. This invention provides a solution to this problem.

This invention relates to a composition that may be used to form a biological indicator. The composition comprises: a host organism comprising a spore forming bacteria; a reporter gene for producing an indicator enzyme; a regulatory gene; and a vehicle for inserting the reporter gene and the regulatory gene in the host organism; the host organism bearing a transposable genetic element in its genome for inserting an insertion sequence in the regulatory gene; the insertion sequence comprising a transposase, a pair of terminal inverted repeat sequences, and at least one open reading frame for expressing the transposase. The vehicle may comprise a plasmid or a viral vector. The vehicle may be taken up by the host organism. The insertion sequence may be inserted in the regulatory gene. The host organism may then undergo sporulation to form the biological indicator. The biological indicator may comprise spores derived from the foregoing composition. While not wishing to be bound by theory, it is believed that the insertion sequence modifies the regulatory gene to allow expression of the reporter gene upon being hydrated without the necessity of employing an inducer. This allows for use of the biological indicator for monitoring the effectiveness of a sterilization without the problems associated with using an inducer.

In an embodiment, the reporter gene comprises bgaB, the regulatory gene comprises xylR, the insertion sequene comprises IS5376, the vehicle is a plasmid, and the host organism comprises *Geobacillus stearothermophilus*.

In an embodiment, the host organism comprises *Geobacillus stearothermophilus*, the host organism containing a plasmid construct, the plasmid constructing comprising the sequence set out in SEQ ID No. 1.

This invention relates to a biological indicator, comprising: a host organism comprising *Geobacillus stearothermophilus*, the host organism containing a plasmid construct, the plasmid construct having the sequence set out in SEQ ID No. 1.

This invention relates to a process, comprising: exposing an article to be sterilized and the above-indicated biological indicator to a sterilization medium.

This invention relates to a process, comprising: exposing an article to be sterilized and the above-indicated biological indicator to a sterilization medium; and detecting the presence of the indicator enzyme to determine the effectiveness of the sterilization. In an embodiment, the indicator enzyme acts upon an enzyme substrate to form an enzyme-modified product. The enzyme-modified product may comprise a luminescent, fluorescent or colored material that can be detected.

This invention relates to a sterilization monitor, comprising: a first compartment containing the above-indicated biological indicator, the first compartment being adapted to permit the biological indicator to be brought into contact with a sterilization medium during a sterilization process; and a second compartment containing a recovery medium, the second compartment being adapted to maintain the recovery medium separate from the biological indicator during the sterilization process, and to permit the recovery medium to contact the biological indicator after the biological indicator has been exposed to the sterilization medium.

BRIEF DESCRIPTION OF THE DRAWINGS

In the annexed drawings, like parts and features have like references.

FIGS. 1A-1B disclose a series of sequence listings for the IS4 family of insertion sequences.

FIGS. 2A-2C disclose a schematic illustration and a series of sequence listings for the IS21 family of insertion sequences.

DETAILED DESCRIPTION

Figure 1A:
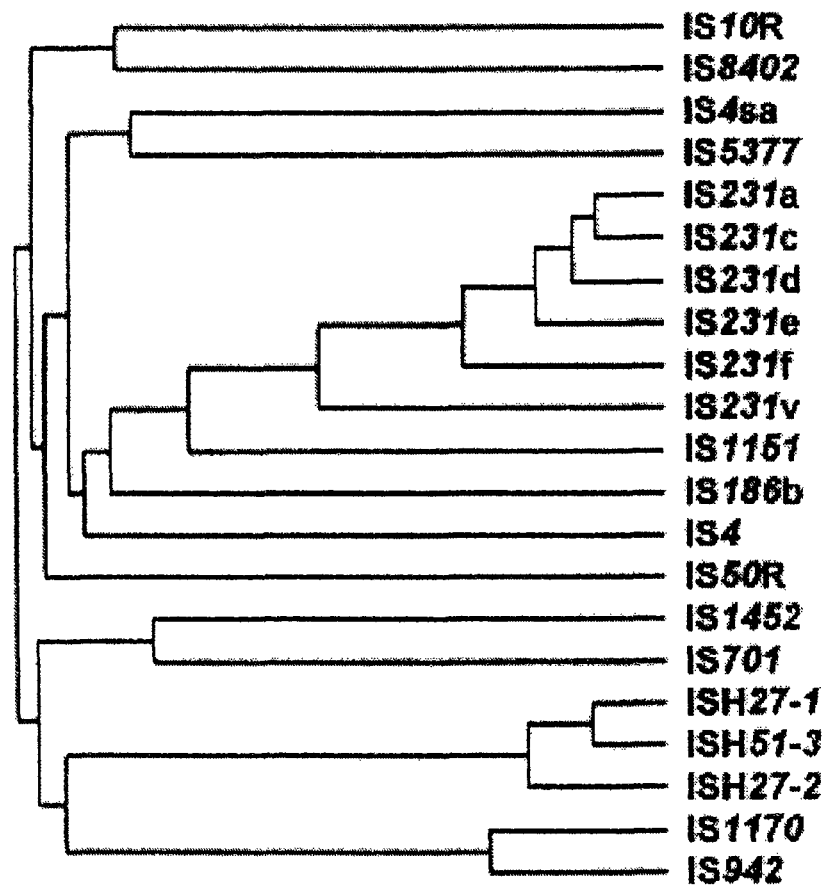

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "sterilization" refers to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term sterilization is used herein to also refer to methods and procedures less rigorous than sterilization, for example, disinfection, sanitization, and the like. The biological indicator and the processes and apparatus described herein may be used in health care fields, scientific fields, and the like. These may be used in commercial and industrial applications where sterilization, disinfection, sanitization, decontamination, cleaning, and the like, may be desired. The commercial and industrial applications may include processes such as food processing, pasteurization, soil remediation, water remediation, and the like.

The term "insertion sequence" (also known as an IS, an insertion sequence element, an IS element, a transposable genetic element, transposon, or jumping gene) refers to a short DNA sequence that acts as a simple transposable element. Insertion sequences typically have two major characteristics: they are small relative to other transposable elements (generally around 700 to 2500 bp in length) and only code for proteins implicated in the transposition activity. They are different from other transposons, which also carry accessory genes such as antibiotic resistance genes.

The term "base pair" or "bp" refers to building blocks of the DNA double helix which contribute to the helical and folded structures of both DNA and RNA. The term "kilobase" or "kb" refers to a unit of measurement equal to 1000 base pairs.

The sterilization process for which the inventive biological indicator may be used may comprise any sterilization process. The sterilization process may include sterilization processes wherein the sterilization medium or sterilant may comprise steam, dry heat, radiation, plasma, as well as one or more gaseous sterilants, one or more liquid sterilants, and the like. The radiation may comprise electron beam or any electromagnetic spectra including ionizing radiation, pulsed white or ultraviolet light, microwave, and the like. The radiation may comprise gamma or beta radiation. The gaseous sterilants may comprise ethylene oxide, gaseous hydrogen peroxide, and the like. The liquid sterilants may comprise formalin (formaldehyde gas dissolved in water and optionally containing methanol to inhibit the formation of toxic substances), glutaraldehyde, peracetic acid, liquid hydrogen peroxide, and the like.

The biological indicator of the present invention may be used to examine the lethality of sterilants against any microorganism with less resistance to the sterilization process than the host organism provided with the inventive biological indicator. These microorganisms may include bacteria such as *Escherichia coli*, *Legionella* sp., *Campylobacter* sp., and other enteric bacteria, as well as *Staphylococcus* and *Streptococcus* species and other human pathogenic microorganisms such as *Cryptosporidium*.

The growth of an organism may comprise the combined result of a multitude of cellular processes. In typical biological indicator applications this may be observed in several ways. As cells grow and divide their individual numbers increase to a point at which the support medium of the cells may change from clear to opaque (turbid). To facilitate this observation of growth, a pH indicator dye may be used. Growth requires energy. This energy may be provided by the ability of the cell to metabolize nutrients contained in the support medium. The breakdown products of this process may cause the support medium to become acidic. This acidity may induce a pH indicator dye (e.g., phenol red) to change color. As a result, growth may be observed as the conversion of the support medium from a clear red to yellow color, for example, to a turbid yellow condition. Although these processes are slow, they represent compelling evidence of life and are generally accepted as the benchmark by the various sterility assurance regulatory bodies.

With the present invention, a biological indicator is provided which is derived from a composition comprising: a host organism comprising a spore forming bacteria; a reporter gene capable of producing an indicator enzyme; a regulatory gene; and a vehicle for inserting the reporter gene and the regulatory gene in the host organism; the host organism bearing a transposable genetic element in its genome for inserting an insertion sequence in the regulatory gene; the insertion sequence comprising a transposase, a pair of terminal inverted repeat sequences, and at least one open reading frame for expressing the transposase. The vehicle, which may comprise a plasmid or a viral vector, is taken up by the host organism. The insertion sequence is inserted in the regulatory gene. The host organism is sporulated to form the biological indicator. Expression of the reporter gene occurs when the reporter gene is hydrated, which can occur when the reporter gene is exposed to a recovery medium. Advantageously, the recovery medium is characterized by the absence of an inducer (e.g., xylose). What may be exposed to the sterilization process are the various and vital mechanisms the host organism uses to survive and grow and which are also used for the production of the indicator enzyme. These may include the DNA polymerases used for cellular growth (and replication of the plasmid or viral vector), RNA polymerases for transcription of the metabolic requirements of the host organism (and the plasmid or viral vector borne reporter gene, e.g., bgaB) and the ribosomal polysomes required for the translation of cellular proteins and expression of the reporter gene. In order to be effective for determining the effectiveness of a sterilization process, the biological indicator should be more resistant to the sterilization than the organisms that are to be destroyed by the sterilization.

The host organism may comprise any spore forming bacteria that bears a transposable genetic element in its genome that is capable of modifying the regulatory gene by inserting an insertion sequence in the regulatory gene. The type of host organism used may be dependent upon a variety of factors exemplified by the type of sterilization process being used. The host organism may comprise bacteria of the Bacillus or Clostridia genera. These may include *Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans*, or a mixture of two or more thereof, and the like. *Geobacillus stearothermophilus* is particularly useful.

*Geobacillus stearothermophilus* is widely distributed in nature. Many species can be isolated from soils and muds. They are also associated with heated materials, such as formation waters of oil fields in Russia, Kazakhstan, and China, and hot springs in Yellowstone National Park. Both *G. stearothermophilus* and *G. kaustophilus* strains have also been isolated from mud samples taken from the Mariana Trench. One *Bacillus* Genetic Stock Center (BGSC) strain was also isolated from rotting wood in Florida, USA.

*Geobacillus stearothermophilus* (NRRL B-1172) may be equivalent to the American Type Culture Collection (ATCC) strain 12980 and strain 26 from the collection of the National Canning Association. This is a thermophilic spore-forming organism with optimal growth conditions between 55-65° C. This particular strain of *Geobacillus stearothermophilus* is a source of the restriction endonuclease BstPI. *Geobacillus stearothermophilus* is classified by ATCC as a Biosafety Level 1 organism, according to U.S. Public Health Service guidelines. It is not known to cause disease in healthy adult humans, animals or plants and is not harmful to the environment.

The vegetative form of *Geobacillus stearothermophilus* is rod-shaped cells that produce one endospore per cell. The cell length ranges from 2.0-3.5 micrometers with a cell width ranging from 0.6-1.0 micrometers. Cells occur either singly or in short chains and are motile by means of peritrichous flagella. The cell wall structure is gram-positive, but the gram stain reaction may vary between positive and negative depending on the age of the culture.

*Geobacillus stearothermophilus* can utilize hydrocarbons ($C_{10}$, $C_{11}$). It will produce acid but no gas upon utilization of glucose, fructose, maltose, mannose and sucrose. Phenylalanine is not deaminated, tyrosine is not degraded, indole is not produced, and the Voges-Proskauer reaction is negative.

*Geobacillus stearothermophilus* is a thermophilic organism whose distinctive diagnostic characteristics include its capacity to grow at 65° C. and a limited tolerance to acid.

The reporter gene may comprise lacZ, bgaB, xylE, cat, gfp, or a mixture of two or more thereof. The term "lacZ" refers to a gene coding for β-galactosidase. The term "bgaB" refers to the gene coding for thermostable β-galactosidase from *G. stearothermophilus*. The term "xylE" refers to gene coding for catechol-2,3-dioxygenase from *Pseudomonas putida*. The term "cat" refers to the gene coding for chloramphenicol acetyltransferase. The term "gfp" refers to the gene for coding thermostable green fluorescent protein variants.

The regulatory gene may comprise xylR, lacI, tetR, or a mixture of two or more thereof. The term "xylR" refers to a regulator of the xylose operon. The term "lacI" refers to a regulator of the lac operon. The term "tetR" refers to a regulator of the tet operon. The thermostable counterparts of these may be used. The regulatory gene may be taken up by the test organism with the same vehicle used to insert the reporter gene in the test organism.

The insertion sequence may be derived from the host organism and added to the regulatory gene. The insertion sequence may comprise an IS4 or an IS21 family insertion sequence. The nomenclature used in Mahillon et al., "Insertion Sequences," Microbiology and Molecular Biology Reviews, 1998, 62(3): 725, is used in this disclosure. The Mahillon et al. article is incorporated herein by reference.

The IS4 family is depicted in FIGS. 1A-B. The insertion sequences of this family comprise a transposase, a pair of terminal inverted repeat sequences (IRs), and a single open reading frame for expressing the transposase. The open reading frame extends along the length of the insertion sequence between the terminal inverted repeat sequences. FIG. 1A is a dendrogram based on alignments of the putative Tpases. The term "Tpase" is an abbreviation for transposase. FIG. 1B discloses terminal IRs of selected members.

The IS4 family of insertion sequences contains 41 members, including 13 isoforms. Many members, such as IS10 and IS50, are involved in compound transposons. Several members carry GATC methylation sites, which, for both IS10 and IS50, may play a modulating role in transposition activity.

IS10 and IS50 may be the best-characterized members of the IS4 family. Both transpose by a "cut-and-paste" mechanism, as does IS231A. IS10 forms part of the composite tetracycline resistance transposon Tn10.

The IS4 family of insertion sequence may comprise IS4, IS10, IS50, IS186, IS231, IS701, IS942, IS1151, IS1170, IS1452, IS5377, IS8402, ISH27-1, ISH27-2 or ISH51-3. IS5377 may be particularly useful.

Figure 2A:
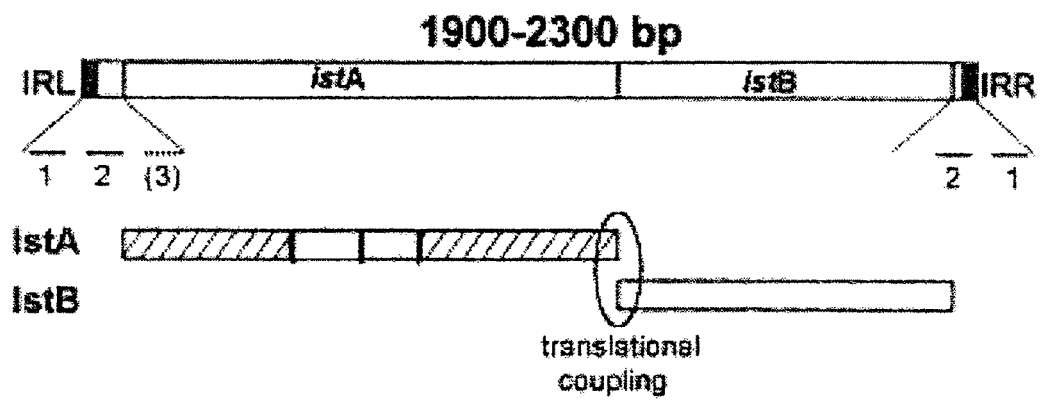
Figure 2B:
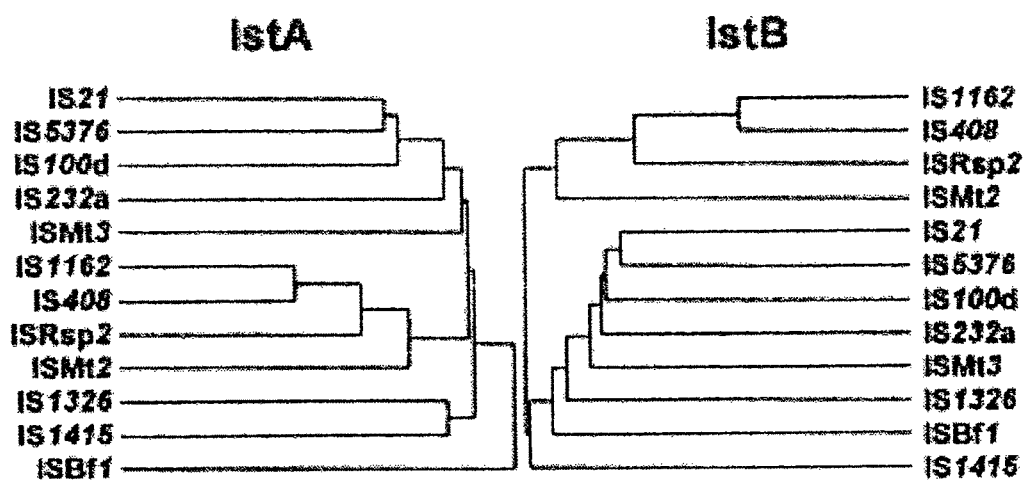

The IS21 family is depicted in FIGS. 2A-2C. The insertion sequences of this family comprise a transposase, a pair of terminal inverted repeat sequences, and two consecutive open reading frames for expressing the transposase. Referring to FIGS. 2A-2C, the IS21 family members have terminal inverted repeat sequences (IRL and IRR) with two consecutive reading frames (istA and istB) positioned between the terminal inverted repeat sequences. The terminal inverted repeat sequences IRL and IRR are shown as solid boxes in FIG. 2A. The position of the istA and istB reading frames is also shown in FIG. 2A. The horizontal lines below show the relative positions of the multiple repeat elements whose sequences are presented in FIG. 2C. IstA (hatched box) together with the potential DDE motif (stippled box) and IstB (open box) are indicated in FIG. 2A. The possibility of translational coupling between the two reading frames is indicated in FIG. 2A. The dendrogram shown in FIG. 2B is derived from the alignment of the istA and istB gene products. Nucleotide sequences of the multiple terminal repeats, together with their coordinates are shown in FIG. 2C. CS (complementary strand) L1, L2, and L3, and R1 and R2, indicate internal repeated sequences at the left and right ends, respectively.

There are 15 distinct members of the IS21 family together with 6 iso-ISs. They carry related terminal IRs whose lengths may vary between 11 bp (IS21) and 50 bp (IS5376) and generally terminate in the dinucleotide 5'-CA-3'. Several members, but not IS21 itself, carry multiple repeated sequences at their ends which include part of the terminal IRs and which may represent Tpase binding sites. Insertion of these elements results in a direct target repeat of 4 bp or 5 bp, while two members (IS53 and IS408) may generate 8 bp. They exhibit two consecutive open reading frames: a long upstream frame designated istA and a shorter downstream frame designated istB (FIG. 2A). The putative IstA and IstB proteins carry several blocks of highly conserved residues. Overall identities range from 10 to 59% for IstA and from 25 to 67% for IstB. The istB frame may be located in a relative reading phase of −1 (e.g., IS21 and IS5376) or +1 (e.g., IS232 and IS1326) compared to istA. It can be slightly separated from istA (17 bp for IS408) or can overlap for 1 bp (IS21) or for several base pairs (IS232, IS5376, and IS1326); it is generally preceded by a potential ribosome binding site. The arrangement of the two reading frames suggests that translational coupling may occur (FIG. 2A).

The IS21 family of insertion sequence may comprise IS21, IS53, IS232A, IS408, IS1162, IS1326, IS1415 or IS5376. IS5376 is a particularly useful insertion sequence.

IS5376 is depicted in SEQ ID No. 1 at coordinates (2060) . . . (4166). IS5376 may be described, using slightly different terminology, as having the following segments:

| | Coordinates in SEQ ID No. 1 |
|---|---|
| 1) First inverted repeat sequence | (2060) . . . (2109) |
| 2) tnpA gene (ATP binding protein) | (2120) . . . (2875) |
| 3) tnpB gene (transposase) | (2872) . . . (4074) |
| 4) RBS (ribosome binding site) | (4082) . . . (4088) |
| 5) Second inverted repeat sequence | (4177) . . . (4166) |

The "tnpA" and "tnpB" genes code for transposases needed by the IS5376 to insert into a new site. The term "ATP-binding protein" refers to a sequence of protein subunits (i.e., genomic DNA base pairs) that promote the attachment of ATP (adenosine-5'-triphosphate) to a target protein.

The vehicle for inserting the reporter gene and the regulatory gene in the host organism may comprise one or more plasmids or one or more viruses (or viral vectors). When added to the host organism, the insertion sequence may be transferred from the host organism to the vehicle. In an embodiment, the insertion sequence is inserted in the regulatory gene. In an embodiment, the regulatory gene is xylR and the insertion sequence is IS5376 which is inserted in the xylR regulatory gene. The vehicle may be referred to as a vector. The plasmids may comprise circular double-stranded DNA that are separate from chromosomal DNA. The plasmids may be linear. The size of the plasmids may be in the range from about 2000 to about 20000 base pairs (bp), or in the range from about 5000 to about 10000 bp. One or more copies (for example, from 1 to about 3000 copies, or from 1 to about 60 copies, or from about 20 to about 3000 copies) of the same plasmid may be taken up by a cell of the test organism. The plasmids may contain one or more DNA sequences that serve as an origin of replication (ori). The plasmids may contain one or more genetic markers. The plasmids may contain a polylinker or multiple cloning site (MCS) which may be a relatively short region containing one or more restriction sites allowing the insertion of DNA fragments. The plasmids may contain one or more genes that provide a selective marker to induce the test organism to retain the plasmid. The selective marker may comprise an antibiotic resistance gene and/or or a gene with nutritional capability. The plasmids may comprise conjugative plasmids which contain tra-genes which perform the process of conjugation, the sexual transfer of plasmids to another bacterium.

Naturally occurring plasmids exist over a broad range of host organisms in nature. They may comprise genes, regulatory elements and/or structural pieces of DNA. Plasmids usually provide some advantage to their host organism (e.g. antibiotic resistance or the ability to use certain nutritional sources of energy) and may be tolerated by their host organisms for as long as this advantageous relationship may exist. Genetically engineered plasmids may comprise a patchwork of genes, regulatory elements and/or structural pieces of interest. Since there are so many naturally occurring (and previously engineered) plasmids available, there is a wide choice of genes to choose from. The genes employed may be selected based on the desired properties of the finished plasmid construct. These properties may include the ability to transform the full range of useful host organisms, provide some selective advantage to the host organism (e.g., antibiotic resistance), produce a thermostable and rapidly detectable signal on demand. This may be accomplished by piecing together (ligation) the required attributes in the form of DNA segments from a variety of source plasmids. For example, the fragments may comprise origins of replication for both gram positive and gram negative organisms, a cat gene for chloramphenicol resistance, a bgaB gene for thermostable β-galactosidase, and an xylR regulator to regulate the bgaB gene product until needed.

A plasmid of specific design may be constructed by assembling the desired genetic elements. The genetic elements may be assembled by restriction digest of the desired genetic sequence from a donor plasmid or organism to produce ends of the DNA which may then be readily ligated to another genetic sequence. Typically, a 5' or 3' overhang may be produced via restriction digest on both sequences targeted for ligation. Following digestion, the target sequences may be purified and then ligated together with an enzyme (ligase). The plasmid may be constructed by assembling a base plasmid containing origins of replication for both gram positive and gram negative organisms as well as a cat gene for chloramphenicol resistance. The regulator gene (e.g., xylR) may be attached to the base plasmid by restriction digest of the base plasmid and ligation of the regulator gene segment. Following confirmation of the proper attachment of the regulator segment to the base segment, the process may be repeated for the reporter gene segment (e.g., bgaB). Upon complete assembly of the genetic elements and confirmation of proper assembly and orientation, the plasmid may be inserted into a host organism. The insertion sequence may be transferred from the host organism and inserted in the plasmid construct at any desired location for which there is a complementary insertion site (e.g., the xylR).

The resulting plasmid may comprise a plasmid construct comprising a reporter gene, regulatory gene and insertion sequence. The plasmid construct may further comprise at least one origin of replication, at least one selectable marker, at least one inducible promoter. The selectable marker may comprise an antibiotic resistance gene and/or a gene with exogenous nutritional capability. These may include chloramphenicol, ampicillin or spectinomycin antibiotic genes, and/or xylose or lactose nutritional genes. The inducible promoter may comprise PxylA. The term PxylA refers to a transcription promoter that requires xylose to remain active. The reporter gene may comprise lacZ, bgaB, xylE, cat, gfp, and the like. The plasmid may comprise two origins of replication. One of the origins of replication may comprise a gram negative origin of replication and the other origin of replication may comprise a gram positive origin of replication. The gram negative origin of replication may comprise *Escherichia coli*. The gram positive origin of replication may comprise *Geobacillus stearothermophilis* or *Bacillus atrophaeus*. The plasmid constructs that may be useful may contain from about 2000 bp to about 20000 bp, or from about 5000 bp to about 15000 bp, or from about 10,000 bp to about 12,000 bp.

Figure 7:
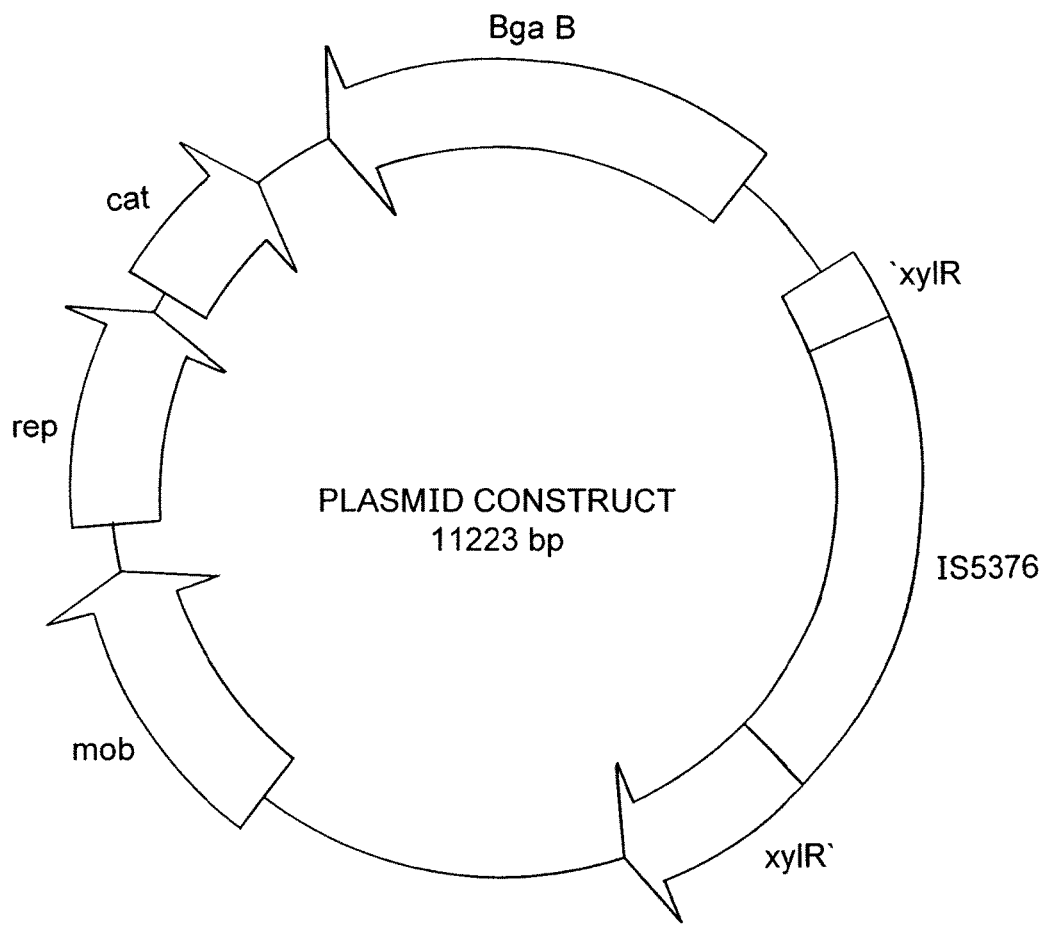
FIG. 7 is a schematic illustration of a plasmid construct containing 11223 base pairs (bp).

The plasmid construct that may be used is illustrated in FIG. 7 and set out in SEQ ID No. 1. This plasmid construct contains 11223 pb. This plasmid construct contains the following segments, which are set out in SEQ ID No. 1 at the indicated coordinates:

| | Coordinates |
|---|---|
| xyIR' - regulatory gene | (1746 ... (2059) |
| IS5376 - insertaiton sequence | (2060) ... (4166) |
| 'xyIR - regulatory gene | (4167) ... (5023) |
| mob - mobility factor gene | (6769) ... (8016) |
| rep - gene for replication | (8245) ... (9249) |
| cat - chloroamphenicol acetyl transferase | (9356) ... (10006) |
| bgaB - reporter gene for producing beta-galactosidase | (1 ... 1196, 10401 ... 11223) |

A complete virus particle, which may be referred to as a virion or a viral vector, may be a gene transporter that comprises nucleic acid surrounded by a protective coat of protein, which may be referred to as a capsid. A capsid may comprise proteins encoded by the viral genome and its shape may serve as a basis for morphological distinction. Virally coded protein units, which may be referred to as promoters, may self-assemble to form the capsid, requiring no input from the virus genome; however, a few viruses may code for proteins which can assist the construction of their capsid. Proteins associated with nucleic acid may be more technically known as nucleoproteins, and the association of viral capsid proteins with viral nucleic acid may be referred to as a nucleocapsid. The viruses may not be considered to be living organisms and may lack the means for self-reproduction outside a host cell. The viruses used herein with bacteria may be referred to as bacteriophages or phages. Examples of the viruses that may be used may include lambda and M13 bacteriophages. The reporter gene, regulatory gene and insertion sequence may be inserted in the virus by first cleaving the non-recombinant phage DNA with an endonuclease and then ligating a piece of DNA to the two newly formed ends.

The vehicle (e.g., plasmid or viral vector) is taken up by the host organism by transformation or conjugation, for example, with plasmids, or transduction or transfection, for example, with viral vectors. Whether using a plasmid or a viral vector as the vehicle for the transformation of the host, the resulting transforming DNA and the genes it contains may remain separate from the host organisms' DNA or may become integrated into the genome of the host organism. The insertion sequence may be inserted in the regulatory gene.

The host organism containing the vehicle may be sporulated to form the biological indicator. Spores are a highly resistant, dormant cell type formed from the spore forming of bacteria. Endospores (or simply spores) form within the vegetative mother cell in response to adverse changes in the environment, most commonly nutrient depletion. The mother cell undergoes an asymmetrical cell division, where it replicates its genetic material, which is then surrounded by multiple concentric and spore specific layers. The mother cell then disintegrates, releasing the mature dormant spore which requires neither nutrients, water nor air for survival and is protected against a variety of trauma, including extremes of temperature, radiation, and chemical assault. These spores are useful as biological indicators for monitoring the effectiveness of sterilization processes.

The indicator enzymes, which may be produced by the reporter gene, may comprise beta-D-galactosidase, beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine am inopeptidase, proline am inopeptidase, tyrosine am inopeptidase, phenylalanine aminopeptidase, beta-D-glucuronidase, fatty acid esterase, or a mixture of two or more thereof. Thermostable counterparts of these may be used.

The enzyme substrate may comprise a substance or mixture of substances which when acted upon by the indicator enzyme is converted into an enzyme-modified product. In general, the enzyme-modified product may comprise a luminescent, fluorescent, or colored material. Alternatively, the enzyme substrate may comprise one or more compounds which when acted upon by the enzyme, may yield a product which reacts with an additional compound or composition to yield a luminescent, fluorescent, or colored material.

There are two basic types of enzyme substrates that may be used for the detection of specific indicator enzymes. The first type of enzyme substrate may be either fluorogenic or chromogenic, and may be given a chemical formula such as, AB. When acted upon by the indicator enzyme, AB, may break down to A+B. B, for example, may be either fluorescent or colored. In one embodiment, two B compounds may react together to produce the fluorescent or colored signal. A specific example of a fluorogenic substrate of this type may be 4-methylumbelliferyl phosphate. In the presence of the indicator enzyme phosphatase, the substrate may be broken down into 4-methylumbelliferone and phosphate. Other fluorogenic substrates of this type may include the derivatives of 4-methylumbelliferyl, 7-amido-4-methylcoumarin, indoxyl and fluorescein. An example of a chromogenic substrate of this type may be 5-bromo-4-chloro-3-indolyl phosphate. In the presence of phosphatase, the substrate may be broken down into indigo blue and phosphate. Other chromogenic substrates of this type may include derivatives of 5-bromo-4-chloro-3-indolyl, nitrophenol and phenolphthalein.

The second type of enzyme substrate may be given by the chemical formula CD, for example, which may be converted by a specific enzyme to C+D. However, neither C nor D may be fluorescent or colored, but D may be capable of being further reacted with compound Z to give a fluorescent or colored compound, thus indicating enzyme activity. A specific fluorogenic example of this type may be the amino acid lysine. In the presence of the enzyme lysine decarboxylase, lysine may lose a molecule of $CO_2$. The remaining part of the lysine may then be called cadaverine, which is strongly basic. A basic indicator such as 4-methylumbelliferone may be incorporated and may be fluoresce in the presence of a strong base. A chromogenic substrate of this type may be 2-naphthyl phosphate. The indicator enzyme phosphatase, may react with the enzyme substrate to yield beta-naphthol. The liberated beta-naphthol may react with a chromogenic reagent containing 1-diazo-4-benzoylamino-2, 5-diethoxybenzene to produce a violet color.

The enzyme substrate may comprise a fluorogenic compound, defined herein as a compound capable of being enzymatically modified, e.g., by hydrolysis, to provide a derivative fluorophore which has an appreciably modified or increased fluorescence.

The fluorogenic compounds may in themselves be either non-fluorescent or meta-fluorescent (i.e., fluorescent in a distinctly different way, e.g., either by color or intensity, than the corresponding enzyme-modified products) and appropriate wavelengths of excitation and detection, may be used to separate the fluorescence signal developed by the enzyme modification from any other fluorescence that may be present.

A number of enzyme substrates for indicator enzymes of diverse origins may be used. These may include fluorogenic 4-methylumbelliferyl derivatives (hydrolyzable to 4-methylumbelliferone); derivatives of 7-amido-4-methylcoumarin; diacetylfluorescein derivatives; and fluorescamine.

Derivatives of 4-methylumbelliferyl that may be used as the enzyme substrate may include: 4-methylumbelliferyl-2-acetamido-4,6-O-benzylidene-2-deoxy-beta-D-lucopyranoside; 4-methylumbelliferyl acetate; 4-methylumbelliferyl-N-acetyl-beta-D-galactosaminide; 4-methylumbelliferyl-N-acetyl-alpha-D-glucosaminide; 4-methylumbelliferyl-N-acetyl-beta-D-glucosaminide; 2'-(4-methylumbelliferyl)-alpha-D-N-acetyl neuraminic acid; 4-methylumbelliferyl-alpha-L-arabinofuranoside; 4-methylumbelliferyl alpha-L-arabinoside; 4-methylumbelliferyl butyrate; 4-methylumbelliferyl-beta-D-cellobioside; methylumbelliferyl-beta-D-N, N'-diacetyl chitobioside; 4-methylumbelliferyl elaidate; 4-methylumbelliferyl-beta-D-fucoside; 4-methylumbelliferyl-alpha-L-fucoside; 4-methylumbelliferyl-beta-L-fucoside; 4-methylumbelliferyl-alpha-D-galactoside; 4-methylumbelliferyl-beta-D-galactoside; 4-trifluoromethylumbelliferyl beta-D-galactoside; 6,8-difluoro-4-methylumbelliferyl-beta-D-galactoside; 4-methylumbelliferyl-alpha-D-glucoside; 4-methylumbelliferyl-beta-D-glucoside; 4-methylumbelliferyl-7,6-sulfo-2-acetamido-2-deoxy-beta-D-glucoside; 4-methylumbelliferyl-beta-D-glucuronide; 6,8-difluor-4-methylumbelliferyl-beta-D-glucuronide; 4-methylumbelliferyl p-guanidinobenzoate; 4-methylumbelliferyl heptanoate; 4-methylumbelliferyl-alpha-D-mannopyranoside; 4-methylumbelliferyl-beta-D-mannopyranoside; 4-methylumbelliferyl oleate; 4-trifluoromethylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl-beta-D-N, N', N'''-triacetylchitotriose; 4'-methylumbelliferyl 2,3,5-tri-beta-benzoyl-alpha-L-arabinofuranoside; 4-methylumbelliferyl-beta-trimethylammonium cinnamate chloride; 4-methylumbelliferyl 4-guanidinobenzoate; and 4-methylumbelliferyl-beta-D-xyloside.

Derivatives of 7-amido-4-methylcoumarin that may be used as the enzyme substrate may include: L-alanine-7-amido-4-methylcoumarin; L-proline-7-amido-4-methylcoumarin; L-tyrosine-7-amido-4-methylcoumarin; L-arginine-7-amido-4-methylcoumarin; L-citrulline-7-amido-4-methylcoumarin; L-leucine-7-amido-4-methylcoumarin; L-methionine-7-amido-4methylcoumarin; L-pyroglutamic acid 7-amido-4-methylcoumarin; L-aspartic acid beta-(7-amido-4-methylcoumarin); L-glutamic acid 1-(7-amido-4-methylcoumarin); L-phenylalanine-7-amido-4-methylcoumarin; and 7-glutaryl-phenylalanine-7-amido-4-methylcoumarin. Peptide derivatives of 7-amido-4-methyl coumarin that may be used as the enzyme substrate may include: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methylcoumarin; N-succinyl-Leu-Tyr-7-amido-4-methylcoumarin; Gly-Pro 7-amido-4-methylcoumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Derivatives of diacetylfluorescein that may be used as the enzyme substrate may include fluorescein diacetate, fluorescein dibutyrate, 2',7'-dichlorofluorescein diacetate, fluorescein di-(beta-D-N-acetygalactosamine), fluorescein di-(beta-D-galactoside), fluorescein mono-(beta-D-galactoside), and fluorescein dilaurate.

Where the indicator enzyme whose activity is to be detected is alpha-D-glucosidase, chymotrypsin or fatty acid esterase, a fluorogenic enzyme substrate that may be used may be 4-methylumbelliferyl-alpha-D-glucoside, 7-glutarylphenylalanine-7-amido-4-methyl coumarin, or 4-methylumbelliferyl heptanoate, respectively. Where the indicator enzyme whose activity is to be detected is alpha-L-arabinofuranosidase, a fluorogenic enzyme substrate that may be used may be 4-methylumbelliferyl-alpha-L-arabinofuranoside. Where the indicator enzyme whose activity is to be detected is beta-D-glucosidase, a fluorogenic enzyme substrate that may be used may be 4-methylumbelliferyl-beta-D-glucoside.

An enzyme substrate that may be used may be a chromogenic compound capable of being enzymatically modified to give a derivative chromophore, or a product which reacts with another compound to give a derivative chromophore, which chromophore has a different or more intense color. The chromogenic compounds may be non-colored or colored in a distinctly different way, e.g., either by color or intensity, than the corresponding enzyme-modified products. Appropriate wavelengths of excitation and detection, in manners well known to users of colorometric instrumentation, may be used to separate the colored signal developed by the enzyme modification from any other color that may be present.

Chromogenic compounds that may be used as enzyme substrates may include 5-bromo-4-chloro-3-indolyl derivatives; nitrophenyl derivatives; indoxyl derivatives; and phenolphthalein derivatives.

Derivatives of 5-bromo-4-chloro-3-indolyl that may be used may include 5-bromo-6-chloro-3-indolyl acetate, 5-bromo-4-chloro-3-indolyl acetate, 5-bromo-4-chloro-3-indoxyl-beta-D-galactopyranoside, 5-bromo-4-chloro-3-indolyl-1,3-diacetate, 5-bromo-4-chloro-3-indolyl-beta-D-fucopyranoside, 5-bromo-4-chloro-3-indolyl-beta-D-glucopyranoside, 5-bromo-4-chloro-3-indolyl-beta-D-glucuronic acid, 5-bromo-4-chloro-3-indolyl phosphate, and 5-bromo-4-chloro-3-indolyl sulfate.

Derivatives of nitrophenyl that may be used may include p-nitrophenol and o-nitrophenol derivatives. These include diethyl-p-nitrophenyl phosphate; di-p-nitrophenyl phosphate; p-nitrophenyl-2-acetamido-2-deoxy-3-O-beta-galactopyranosyl-beta-glucopyranoside; p-nitrophenyl-2-acetamido-2-deoxy-beta-glucopyranoside; p-nitrophenyl acetate; p-nitrophenyl-N-acetyl-beta-D-glucosaminide; p-nitrophenyl-beta-D-N, N'-diacetylchitobioside; p-nitrophenyl-alpha-glucopyranoside; p-nitrophenyl-alpha-maltoside; p-nitrophenyl-beta-maltoside; p-nitrophenyl-alpha-mannopyranoside; p-nitrophenyl-beta-mannopyranoside; p-nitrophenyl myristate; p-nitrophenyl palmitate; p-nitrophenyl phosphate; bis(p-nitrophenyl)phosphate; tris(p-nitrophenyl)phosphate; p-nitrophenyl-beta-glucopyranoside; p-nitrophenyl-beta-glucuronide; alpha-p-nitrophenylglycerine; p-nitrophenyl-alpha-rhamnopyranoside; p-nitrophenyl stearate; p-nitrophenyl sulfate; p-nitrophenyl-2,3,4,6-tetra-O-acetyl-beta-glucosaminide; p-nitrophenyl thymidine mono-phosphate; p-nitrophenyl-2,3,4-tri-O-acetyl-beta-glucuronic acid methyl ester; and p-nitrophenyl valerate.

Useful o-nitrophenols may include o-nitrophenyl acetate, o-nitrophenyl-beta-glucoside and o-nitrophenyl-beta-D-glucopyranoside. Other useful nitrophenyl derivatives may include nitrophenyl-beta-fucopyranoside; nitrophenyl-alpha-galactopyranoside; nitrophenyl-beta-galactopyranoside; nitrophenyl butyrate; nitrophenyl caprate; nitrophenyl caproate; nitrophenyl caprylate; nitrophenyl laurate; and nitrophenyl propionate.

Indoxyl derivatives that may be used may include indoxyl-acetate; indoxyl beta-D-glucoside; 3-indoxyl sulfate; and 3-indoxyl phosphate.

Phenolphthalein derivatives that may be used may include: phenolphthalein dibutyrate; phenolphthalein diphosphate; phenolphthalein disulfate; phenolphthalein glucuronic acid; phenolphthalein mono-beta-glucosiduronic acid; phenolphthalein mono-beta-glucuronic acid; and phenolphthalein mono-phosphate.

The above-described chromogenic enzyme substrates may react directly with an appropriate indicator enzyme to produce a chromophore.

Additional enzyme substrates containing 1-naphthyl, 2-naphthyl and Napthyl-AS-BI derivatives may be employed if the derivative enzyme modified product is further reacted with a chromogenic reagent, such as diazotized dyes, e.g., 1-diazo-4-benzoylamino-2, 5-diethoxybenzene, 1-diazo-4-benzoylamino-2, 5-diethoxybenzene, p-diazo-2,5-diethoxy-N-benzoyalanine, 4-chloro-2-methylbenzene diazonium chloride, and o-aminoazotoluene diazonium salt, to produce a chromophore.

Derivatives of 1-napthyl that may be used may include 1-naphthyl-N-acetyl-beta-D-glucosaminide.

Derivatives of 2-naphthyl that may be used may include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine 2-naphthyl-amine; 2-naphthyl-phosphate; 6-Br-2-naphthyl-alpha-D-galacto-pyranoside; 2-naphthyl-beta-D-galacto-pyranoside; 2-naphthyl-2-D-glucopyranoside; 6-bromo-2-naphthol-beta-D-glucopyranoside; 6-bromo-2-naphthyl-2-D-mannopyranoside; and 2-naphthyl-alpha-L-fucopyranoside.

Derivatives of naphthyl-AS-BI that may be used may include naphthyl-AS-BI-phosphate; and naphthyl-AS-BI-beta-D-glucuronide.

Where the indicator enzyme whose activity is to be detected is alpha-D-glucosidase, the enzyme substrate may be p-nitrophenyl-alpha-glucopyranoside. Where the indicator enzyme whose activity is to be detected is alpha-L-arabinofuranosidase, the enzyme substrate that may be used may be p-nitrophenyl-alpha-L-arabinofuranoside. Where the indicator enzyme whose activity is to be detected is β-galactosidase, the enzyme substrate may be 5-bromo-4-chloro-3-indolyl-β-D-galactopyranoside or 4-methylumbelliferone-β-D-galactopyranoside.

The enzyme substrate that may be used may depend upon the identity of the indicator enzyme whose activity is under study. Below is a list of a number of enzyme substrates, and corresponding indicator enzymes which may react with the enzyme substrate to produce a product having appreciably modified or increased fluorescence or color.

| Enzyme Substrate | Indicator Enzyme |
| --- | --- |
| 4-Methylumbelliferyl acetate | Esterase |
| 4-Methylumbelliferyl butyrate | Esterase |
| 4-Methylumbelliferyl elaidate | Lipase |
| 4-Methylumbelliferyl-β-D-galactopyranoside | β-D-Galactosidase |
| 4-Methylumbelliferyl-α-D-galactopyranoside | α-D-Galactosidase |
| 4-Methylumbelliferyl-α-D-glucopyranoside | α-D-Glucosidase |
| 4-Methylumbelliferyl-β-D-glucopyranoside | β-D-Glucosidase |
| 4-Methylumbelliferyl heptanoate | Esterase |
| 4-Methylumbelliferyl oleate | Lipase |
| 4-Methylumbelliferyl phosphate | Acid or Alkaline Phosphatase |
| 4-Methylumbelliferyl propionate | Esterase |
| 4-Methylumbelliferyl-β-D-galactoside | β-D-Galactosidase |
| 4-Methylumbelliferyl-β-D-glucoside | β-D-Glucosidase |
| 4-Methylumbelliferyl-α-D-glucoside | α-D-Glucosidase |
| 4-Methylumbelliferyl-α-L-arabinofuranoside | α-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | α-D-Galactosidase |
| p-Nitrophenyl phosphate | Alkaline or Acid phosphatase |
| p-Nitrophenyl acetate | Lipase |
| o-Nitrophenyl-β-D-galactopyranoside | β-D-Galactosidase |
| p-Nitrophenyl-α-D-galactopyranoside | α-D-Galactosidase |
| o-Nitrophenyl-β-D-glucopyranoside | β-D-Glucosidase |
| p-Nitrophenyl-α-D-glucopyranoside | α-D-Glucosidase |
| p-Nitrophenyl-β-D-glucuronide | β-D-Glucuronidase |
| p-Nitrophenyl-α-L-arabinofuranoside | α-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate diNa salt | Alkaline Phosphatase |
| Phenolphthalein dibutyrate | Esterase |
| Phenolphthalein diphosphate | Acid or Alkaline phosphatase |
| Phenolphthalein diphosphate pentaNa salt | Acid or Alkaline phosphatase |
| Phenolphthalein-β-D-glucuronide Na salt | β-D-Glucuronidase |
| Phenolphthalein-β-D-glucuronide | β-D-Glucuronidase |
| L-Phenylalanine ethylester HCl | Chymotrypsin |
| Phenyl-β-D-galactopyranoside | β-D-Galactosidase |
| Phenyl-β-D-glucuronide | β-D-Glucuronidase |
| Phenyl-β-D-glucopyranoside | β-D-Glucosidase |
| Phenyl-β-D-glucuronide | β-D-Glucuronidase |
| Phenyl-α-D-glucoside | α-D-Glucosidase |
| Sodium β-glycerophosphate | Acid or Alkaline phosphatase |
| Sodium 1-naphthyl phosphate | Acid or Alkaline phosphatase |

-continued

| Enzyme Substrate | Indicator Enzyme |
|---|---|
| Sodium 2-naphthyl phosphate | Acid or Alkaline phosphatase |
| 2-Naphthyl-butyrate | Esterase |
| β-Naphthyl acetate | Lipase |
| 6-Br-2-naphthyl-β-D-glucoside | β-D-Glucosidase |
| L-Leucyl-2-naphthylamide aminopeptidase | Leucine |
| L-Valyl-2-naphthylamide aminopeptidase | Valine |
| N-glutaryl-phenylalanine-2-naphthylamine | Chymotrypsin |
| Naphthyl-AS-BI-phosphate | Phosphohydralase |
| Indoxyl acetate | Lipase |
| N-Methylindoxyl acetate | Lipase |
| N-Methylindoxyl myristate | Lipase |
| 5-Bromoindoxyl acetate | Lipase |
| 3-Indoxyl phosphate | Acid or Alkaline phosphatase |
| Indoxyl-β-D-glucoside | β-D-Glucosidase |
| 5-Br-4-Cl-3-Indolyl acetate | Lipase |
| 5-Br-4-Cl-3-Indolyl phosphate | Alkaline or Acid phosphatase |
| 5-Br-4-Cl-3-Indolyl-β-D-glucuronic acid | β-D-Glucuronidase |
| Diacetylfluorescein | Lipase/esterase |

Where the indicator enzyme is β-galactosidase, the enzyme substrate may comprise 5-Bromo-4-chloro-3-indolyl-β-D-galactopyranoside (X-gal), 5-Bromo-6-chloro-3-indolyl-β-galactopyranoside (Mag-gal), 5-Bromo-3-indolyl-β-D-galactopyranoside (Bluo-gal), 6-Bromo-2-naphthyl-β-D-galactopyranoside, 6-chloro-3-indolyl-β-D-galacotpyranoside (Rose-gal), 3-Indoxyl-β-D-galactopyranoside (Y-gal), 5-Iodo-3-indoxyl-β-D-galactopyranoside, N-methylindoxyl-β-D-galactopyranoside, 2-Nitrophenyl-β-D-galactopyranoside (ONPG), 4-Nitrophenyl-β-D-galactopyranoside (PNPG), Phenyl-β-D-galactopranoside (P-gal), 2-Chloro-4-nitrophenyl-β-D-lactoside, 4-methylumbelliferyl-β-D-galactopyranoside, 4-trifluoromethylumbelliferyl-β-D-galactopyranoside, Fluorescein di(β-D-galactopyranoside) (FDG), Fluorescein mono-β-D-galactopyranoside, Fluorescein di-(β-D-acetyl galactosamine), 4-Methylumbelliferyl-β-D-lactopyranoside, 2-Napthyl-β-D-galactopyranoside, 8-Hydroxyquinoline-β-D-galactopyranoside, Resorufin β-D-galactopyranoside, 3-Carboxyumbelliferyl-β-D-galactopyranoside, 4-Chloromethyl-6,8-difluoroumbelliferyl-β-D-galactopyranoside, 6,8-Difluor-4-methylumbelliferyl-β-D-galactopyranoside, 6,8-Difluoro-4-heptadecylumbelliferyl-β-D-galactopyranoside, 5-(Pentafluorobenzoylamino)-fluorescein-β-D-galactopyranoside, $C_2$-fluorescein-β-D-galactopyranoside, $C_8$-fluorescein-β-D-galactopyranoside, $C_{12}$-fluorescein-β-D-galactopyranoside, 5-Chloromethylfluorescein-β-D-galactopyranoside, $C_{12}$-resorufin-β-D-galactopyranoside, 7-Hydroxyl-9H-(1,3-dichlor-9,9-dimethylacridin-2-one) (DDAO), or a mixture of two or more thereof.

After the sterilization process has been completed, the biological indicator may be contacted with or placed in a recovery medium containing a nutrient growth media and an enzyme substrate. The recovery medium may comprise an aqueous medium or aqueous solution that provides for germination, metabolism and subsequent grow out of organisms as required. The aqueous medium or aqueous solution may be buffered. If the biological indicator survives the sterilization, the indicator enzyme acts upon the enzyme substrate resulting in the formation of the enzyme-modified product having a detectable color or fluorescence.

The inventive biological indicator may be exposed to a sterilization medium during a sterilization process using any suitable procedure. This may be effected using a sterilization monitor containing the biological indicator. The sterilization process may comprise any sterilization process. The biological indicator is exposed to a sterilization medium during the sterilization process, and then to the recovery medium to determine whether the sterilization process was effective. The sterilization medium may comprise a gaseous or liquid sterilant, dry heat, radiation, and the like. The biological indicator along with the articles to be sterilized are exposed to the sterilization medium during the sterilization process. Upon completion of the sterilization process, the biological indicator is combined with the recovery medium. The biological indicator is then incubated in the presence of the recovery medium for a desired period of time and examined to determine whether the sterilization process was effective. The inventive biological indicator may be used in a sterilizer to test and validate the performance of the sterilizer and/or sterilization cycle to determine whether the sterilizer or sterilization cycle is effective.

The sterilization monitor may be a self-contained sterilization monitor comprising a container with two separate compartments. One of the compartments may contain the biological indicator. The other compartment may contain the recovery medium. In use, the sterilization monitor and the articles to be sterilized are exposed to the sterilization medium. Following sterilization, the sterilization monitor is activated so that the biological indicator comes into contact with the recovery medium sufficiently to determine whether the sterilization process is effective. The sterilization monitor may be used with any sterilization process wherein the biological indicator is exposed to the sterilization medium, for example, sterilization processes employing gaseous sterilants.

Figure 3:
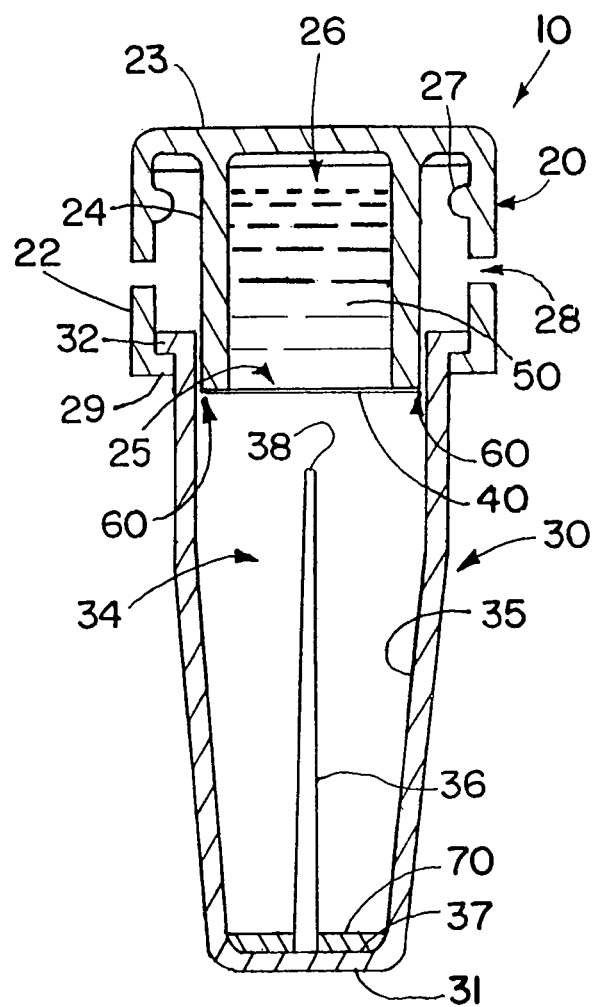
FIG. 3 is a schematic illustration of a sterilization monitor suitable for use with the present invention, the sterilization monitor being shown in a pre-activated configuration.
Figure 4:
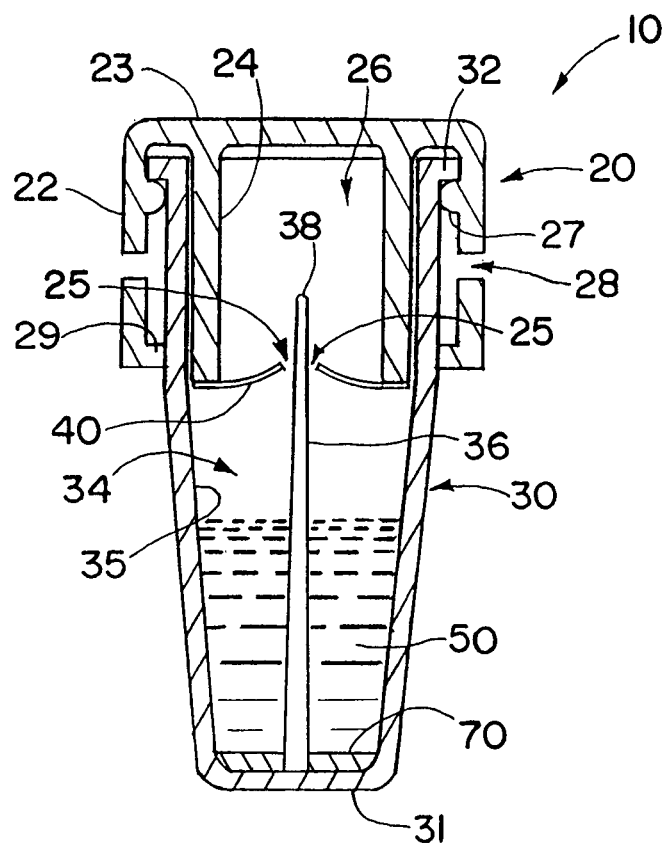
FIG. 4 is a schematic illustration of the sterilization monitor of FIG. 3 in an activated configuration.

Referring to FIGS. 3 and 4, a sterilization monitor 10 is disclosed. The sterilization monitor 10 includes cap 20 that is mounted on container 30. Container 30 includes a closed bottom end 31, an open upper end, and interior space 34. The cap 20 has an outer wall 22, an open lower end, and a closed upper end 23. The cap 20 also includes an inner wall 24, and an inner chamber 26. The inner chamber 26 includes an opening 25 adjacent to the bottom end of the wall 24. The inner chamber 26 contains a growth medium 50. The cap 20 includes a breakable barrier 40 covering the opening 25 and encapsulating the growth medium 50 within the chamber 26. The sterilization monitor 10 is configured for the cap 20 to be mounted to the container 30 in a snap-fit relationship. In other embodiments, not shown, the sterilization monitor 10 may be configured for the cap 20 to be mounted to the container 30 in a threaded relationship in which the cap 20 is engaged with the container 30 by threads and the system is activated by rotating the cap 20 with respect to the container 30, i.e., screwing the cap 20 further onto the container 30.

The container 30 includes an annular projection 32 forming a ridge or lip adjacent or near the upper end of the container 30. The cap 20 includes an annular projection 29 forming a ridge or lip adjacent the bottom of the cap 20. The cap 20 may be mounted onto the container 30 by sliding the ridge 29 of the cap over the ridge 32 of the container. The ridge 32 of the container 30 engages the ridge 29 on the cap 20 to prevent the cap 20 and container 30 from decoupling. The cap 20 and container 30 may be sized such that the ridge 32 exerts a sufficient amount of pressure against the cap 20 to prevent the cap 20 from sliding downward without applying an external downward force to the cap 20.

The container 30 includes one or more puncture members 36 which is adapted to break or puncture breakable barrier 40 when the cap 20 is moved downward, and the barrier 40 contacts the point 38 of puncture member 36. The puncture member 36 is shown as extending upwardly from bottom wall 37 of container 30. In another embodiment, not shown, puncture member 36 may extend upwardly from side wall 35, or from both the side wall 35 and bottom wall 37.

To evaluate a sterilization process, a calibrated concentration of the inventive biological indicator is positioned within the interior 34 of the container 30. The biological indicator may be positioned directly on the walls 35 of the container or provided on a support member (e.g., support member 70) that is positioned within the container 30. The inner chamber 26 is filled with recovery medium 50. The sterilization monitor 10 is then assembled by mounting the cap 20 on the container 30. The cap 20 may be mounted by snap-fitting the cap 20 onto the container 30 as described above, or, for example, by a threaded mounting. With reference to FIG. 3, the cap 20 is mounted on the container 30 in a first, non-activated (or open) position such that the breakable barrier 40 remains intact and is not punctured by the puncture member 36.

With the sterilization monitor 10 assembled such as shown in FIG. 3, the sterilization monitor 10 then can be subjected to a sterilization process. The cap 20 has apertures 28 through which a sterilant vapor enters the sterilization monitor 10. The sterilant enters the cap through the apertures 28 (into the space between the wall 22 and the wall 24) and flows into the container 30 through a space 60 defined between the exterior surface of the inner wall 24 of the cap 20 and the inner surface of the wall 35. The sterilant vapor flows into the container 30 and contacts the biological indicator.

After the sterilization process is completed, the sterilization monitor 10 may be activated by moving the cap 20 downward toward the container 30 to a second (or closed or activated) position, which is illustrated in FIG. 4. The cap 20 is moved downward by applying a sufficient downward force or pressure on the cap 20. As the cap 20 is moved downward, the breakable barrier 40 is brought into contact with the point 38 of puncture member 36, and eventually moved into a position such that the point 38 punctures the breakable barrier 40. When the breakable barrier 40 is punctured, the growth medium 50 drains into the interior space 34 of the container 30 and contacts the biological indicator. It may be desirable to move the cap 20 downward with a twisting motion to effect a greater or maximum opening of the breakable barrier 40 to ensure complete drainage of the inducer fluid into the container.

The inner surface of the cap 20 includes a second annular projection 27. The cap 20 may be moved downward to a position such that the upper portion of the projection 27 engages the bottom of ridge 32 of the container 30 to hold the cap 20 in a second, closed/activated position. The closed/activated position holds the cap 20 in a sealed relationship with the container 30. The sterilization monitor 10 is then incubated for a sufficient period of time to allow microorganism viability to be determined. During incubation, any viable microorganisms from the biological indicator will metabolize and grow. This metabolism and growth releases byproducts into the recovery medium 50. The byproducts may be detected by any selected property including, for example, pH change, color change, opacity, fluorescence, and the like.

In another embodiment, the cap 20 does not include the second projection 27 to maintain the container in the closed position. The container 30 may include another annular projection or a set of detents (not shown) on the outside of the container 30 and located below the ridge 32, which projection or detents may be adapted to engage the ridge 29 on the cap to maintain the container 30 in a closed position. U.S. Pat. No. 5,770,393 illustrates such a configuration, and this patent is incorporated herein by reference for its teachings relating to configurations of cap and container.

In another embodiment, the inner surface of the cap 20 and the outer surface of the container 30 may be threaded, and the cap 20 may be moved into and maintained in a closed position by screwing the cap 20 onto the container 30, in which the cap 20 may be threaded as shown, e.g., in U.S. Pat. No. 8,173,388 B2, which is incorporated herein by reference.

The cap 20, in the embodiment illustrated in FIGS. 3 and 4 is shown as having the aperture 28 to allow for the ingress of sterilant into the sterilization monitor 10. It will be appreciated, however, that the cap 20 need not be provided with such a feature. The number, size, shape, and/or location of the aperture(s) may be selected as desired, with consideration of the particular sterilant with which the sterilization indicator is to be used. For example, the location, shape, and size of the apertures in the cap 20 and/or the container 30 may be selected to provide a tortuous path for the entrance and exit of the sterilization medium between the biological indicator and the surrounding environments. In another embodiment, the space between the side wall of the cap 22 and the outer wall of the vial 30 may be sufficient to provide a torturous path without having to provide an aperture in either the cap or the vial. The tortuous path may also serve to inhibit or prevent contamination from external agents, and to make certain that an adequate amount of sterilant is available. By including the tortuous path, it is more likely that the entire load will be exposed to the sterilant thereby killing any extant microorganisms before the test organism in the sterilization monitor 10 is killed.

Apertures may be provided in the container 30 in addition to or as an alternative to providing apertures in the cap 20. Additionally, if apertures are provided in the container 30, they may be located such that the growth medium 50 does not leak or spill out through such apertures when the sterilization monitor 10 is activated and the barrier 40 is broken.

Figure 5:
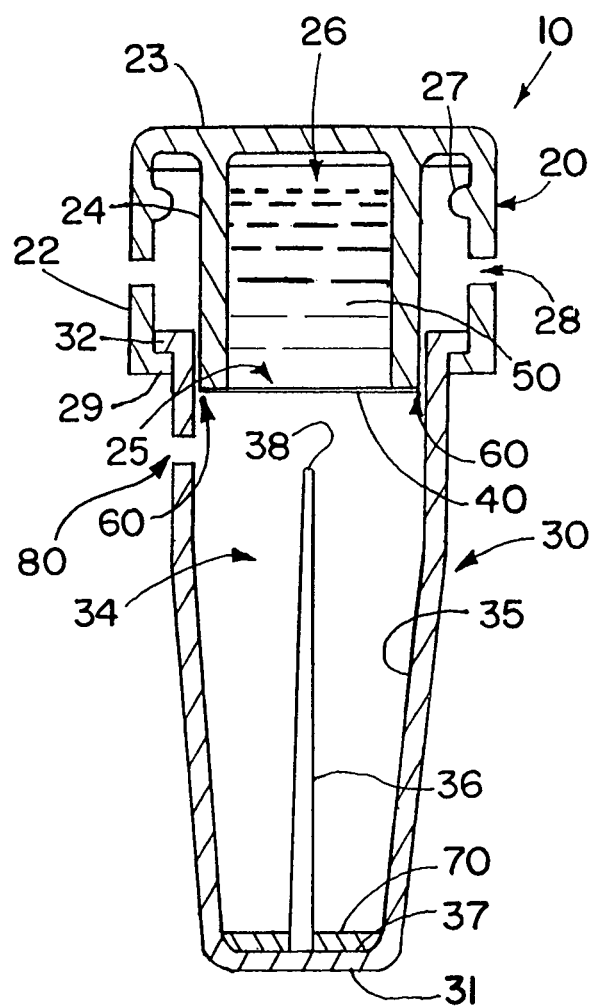
FIG. 5 is a schematic illustration of another embodiment of a sterilization monitor suitable for use with the present invention, the sterilization monitor being shown in pre-activated configuration.

FIG. 5 depicts sterilization monitor 10 in which an aperture 80 is formed in the sidewall 35 of the container 30 at an appropriate position, in addition to the apertures 28 in the cap 20. The aperture 80 shown in FIG. 5 is in the sidewall 35 of the container 30 near the top of the container 30, in the vicinity of the point 38 of the puncture member 36, to avoid leakage or spilling after activation. As can be seen from FIG. 5, after activation, the aperture 80 at this location will be covered by the cap 20 in the activated position. It is noted that the sterilization monitor 10 shown in FIG. 5 includes the aperture 28 in the cap 20, but this may not be necessary. In one embodiment (not shown), the container 30 includes the aperture 80 and is used with a cap similar to the cap 20, but which does not include the aperture 28. Thus, an aperture can be provided either in the cap 20 or in the container 30, or in both the cap 20 and the container 30. Alternatively, no aperture may be required so long as a pathway is provided between the cap 20 and container 30 while in the unactivated state.

After the sterilization process has been completed, the cap 20 is pressed or twisted downward such that the point 38 of the puncture member 36 penetrates and breaks the breakable barrier 40 releasing the recovery medium 50 in the space 26 to mix with and incubate any of the microorganisms of the biological indicator that may have survived the sterilization process.

The recovery medium may comprise an aqueous medium or aqueous solution that includes an enzyme substrate and provides for germination, metabolism and subsequent grow out of organisms as required. The recovery medium may be buffered. The indicator enzyme (e.g., beta-galactosidase), if present as a result of having been produced by the reporter gene in any surviving biological indicator microorganisms, may act upon the enzyme substrate to form an enzyme-modified product which can be detected.

The recovery medium may comprise a lysogeny broth (LB). LB broth is a nutritionally rich medium used for the growth of bacteria. An example of an LB broth that may be used is as follows:

| | |
|---|---|
| Deionized water | 800 mL |
| NaCl | 10 g/l |
| Tryptone | 10 g/l |
| Yeast extract | 5 g/l |
| Deionized water to provide final volume of 1 liter 5N NaOH to adjust pH to 7.0 | |

The pH of the recovery medium may be in the range from about 5 to about 9.5, or about 6.5 to about 7.5, or about 7.0.

The concentration of enzyme substrate in the recovery medium may be dependent upon the identity of the enzyme substrate and the indicator enzyme, the amount of enzyme-modified product that must be generated to be detectable, either visually or by instrument, and the amount of time required to determine whether indictor enzyme is present. The amount of enzyme substrate that may be sufficient may be the amount needed to react with any indicator enzyme that may be present after the sterilization has been completed such that an enzyme-modified product at a molar concentration of at least about $10^{-15}$ molar may be produced within a period of up to about 4 hours, or a molar concentration of at least about $10^{-8}$ molar within a period up to about 2 hours.

The recovery medium may be combined with the biological indicator after the biological indicator has been subjected to the sterilization cycle. The recovery medium containing the biological indicator can then be incubated. Incubation may be continued for a period of time and under conditions sufficient to liberate a detectable amount of the indicator enzyme, assuming any of the biological indicator remains functional. In general, the amount of indicator enzyme which may be detectable may be as low as about $1\times10^{-15}$ molar. The incubation conditions may be sufficient to generate at least about $1\times10^{-8}$ molar of indicator enzyme, or from about $1\times10^{-6}$ to about $1\times10^{-5}$ molar of indicator enzyme. The incubation time and temperature needed to produce a detectable amount of indicator enzyme may depend upon the identity of the indicator enzyme, and the concentration of the indicator enzyme in the growth medium. The incubation temperature may be in the range from about 20° C. to about 70° C. The incubation time may be in the range up to about 4 hours, or in the range from about 0.01 to about 4 hours, or in the range from about 0.01 to about 3 hours, or in the range from about 0.01 to about 2 hours, or in the range from about 0.01 to about 1 hour. The indicator enzyme acts upon the enzyme substrate to form an enzyme-modified product which can be detected. Detection can be achieved within a period of time of up to about 4 hours, or about 0.01 to about 4 hours, or about 0.01 to about 3 hours, or about 0.01 to about 2 hours, or about 0.01 to about 1 hour, or about 0.01 to about 0.7 hour, or about 0.01 to about 0.5 hour.

Generally applicable methods for detecting the enzyme-modified product may include photometric, potentiometric, gravimetric, calorimetric, conductometric, or amperometric techniques. Fluorometric or spectrophotometric methods may be used.

The biological indicator, although herein described primarily in terms of a single indicator enzyme, may provide a plurality of indicator enzymes. For example, the biological indicator may provide three types of indicator enzymes, one enzyme being resistant to heat, a second being resistant to gaseous sterilizing media, and a third being resistant to radiation, e.g., gamma or beta irradiation.

This invention provides a number of advantages over the prior art. These may include sourcing an enzyme (e.g., beta galactosidase) solely on the basis of signal generation strategy. By limiting the role of the indicator enzyme to signal generation, the need to match or correlate the susceptibility of the indicator enzyme to that of the host organism may be eliminated.

Advantages of using the inventive biological indicator include providing results of whether the sterilization is effective within a relatively short period of time in the range up to about 4 hours, or in the range from about 0.01 to about 4 hours, or in the range from about 0.1 to about 3 hours, or in the range from about 0.1 to about 2 hours, or in the range from about 0.2 to about 1 hour. By virtue of the use of the inventive biological indicator, it may be possible to measure the viability of a host organism directly, rather than by indirect measurement of a surrogate molecule. The use of the biological indicator may not be limited to any particular method of sterilization. That is, the biological indicator may be used for any sterilization process. The effectiveness of a sterilization process may be determined using the inventive biological indicator without requiring grow out to provide final confirmation of the effectiveness of the sterilization. By using the disclosed biological indicator, it may not be necessary to employ an electrochemical sensor to determine whether the sterilization is effective, although more rapid results with a sensor may be possible. The biological indicator may be amendable to use with instant read applications such as chip or sensor applications. The biological indicator may be used with any sterilization process employing a most resistant organism, clinically significant organism or bio-warfare organism.

The use of the inventive biological indicator for detecting the effectiveness of a sterilization process may involve the use of measurement based on a genetic theory model (only a living cell can express a gene). The biological indicator may respond to any lethal event or combination of lethal events (transcription, translation, etc.). The biological indicator may provide a fast acting response to any biocidal mode of action (steam, peracetic acid, ethylene oxide, liquid formaldehyde, gaseous formaldehyde, stabilized liquid hydrogen peroxide, vaporous hydrogen peroxide, dry heat, ozone, ortho-phthalaldehyde, gluteraldehyde, chloramines, quaternary amines, phenolics, iodophores, ionizing radiation, ultraviolet radiation, pulsed white light, plasma, microwave radiation, etc.).

The plasmid construct illustrated in FIG. 7 and set out in SEQ ID No. 1 comprises a base plasmid with a disrupted xylR regulatory gene segment, a bgaB reporter gene segment, and an insertion sequence. The insertion sequence is IS5376, which is inserted in the xylR regulatory gene segment. Referring to FIG. 7 and SEQ ID No. 1, mob, cat and rep are part of the original base plasmid. Mob (mobility factor gene) may enhance mobility of the plasmid between hosts via conjugation. Cat (chloroamphenicol acetyl transferase) may provide selective pressure to ensure that the host cells that grow include the plasmid. Rep is a gene for replication. The plasmid construct may be constructed by ligation of an intact xylR regulatory gene segment to the base plasmid. Following successful attachment of the xylR regulatory gene segment to the base plasmid, the process may be repeated for the bgaB reporter gene segment. The plasmid construct may be taken up by *Geobacillus stearothermophilus*, which functions as a host organism. The host organism may modify the xylR regulatory gene segment by inserting the insertion sequence IS5376 in the xylR regulatory gene segment. The plasmid construct may contain 11223 base pairs. The host organism may then be sporulated to form a biological indicator.

Example 1

*Geobacillus stearothermophilus* (NRRL B-1172, also known as ATCC 12980) is the recipient organism and acts as a host for insertion of the plasmid construct illustrated in FIG. 7 and set out SEQ ID No. 1 (hereinafter sometimes referred to as the SEQ ID No. 1 plasmid construct). The *Geobacillus stearothermophilus* is chemically transformed by a modification of the common processes described in Sambrook et al. (Molecular Cloning a laboratory manual—3rd edition). The resulting transformant bears from 5 to 50 copies of the SEQ ID No. 1 plasmid construct, depending on culture conditions in the laboratory, and is stable indefinitely in the presence of selective pressure. The transformed cells are propagated in the presence of the antibiotic chloramphenicol to ensure the selection of the transformed state and then sporulated, cleaned and dispensed into a Self Contained Biological Indicator (SCBI). Spores prepared in this manner are stable in the absence of a selective antibiotic during storage and through to their use in the SCBI. Once removed from selective pressure and allowed to germinate, the vegetative form of these cells reverts to their original phenotypic sensitivity to chloramphenicol within four passages on plates not containing the antibiotic. With the exception of the plasmid, the spores remain equivalent to their wild-type counterparts in all other ways including resistance to steam sterilization.

The SEQ ID No. 1 plasmid construct is made up of fragments from a pre-existing plasmid and DNA from three donor cells. The plasmid vector backbone is originally obtained from a donor plasmid pNW63. The donor plasmid pNW63 is derived in whole from its precursor pNW33N after a duplicated fragment has been removed. The donor plasmid pNW63 is the source for the necessary mobility (mob), replication (rep) and chloramphenicol resistance (cat) genes used in the construction of the SEQ ID No. 1 construct. The original plasmid pNW33N, is a fifth generation vector that stably replicates in *Geobacillus stearothermophilus*. The donor plasmid pNW63 is obtained from the *Bacillus* Genetics Stock Center (BGSC) in an *E. coli* host strain JM109. It features a large multiple cloning site and encodes a thermostable chloramphenicol acetyltransferase variant that is expressed in both gram-positive and gram-negative lab strains.

In addition to the plasmid DNA described above, three additional DNA elements are donated from other organisms. Terminators (T1T2) are derived from the rrnB gene of *Escherichia coli* K12. The reporter element is derived from the bgaB gene and is donated by *Bacillus stearothermophilus* (subsequently reclassified as *Geobacillus kaustophilus*). The expression module xylR comes from the xylose-utilization operon of the non-pathogenic *Bacillus megaterium* strain DSM319.

The remaining DNA segments making up the SEQ ID No. 1 plasmid construct are non-coding, miscellaneous structural features carried over from previous hosts and constructs. They are desirable in that they provide structural integrity, engineered restriction sites and help maintain appropriate open reading frames.

Once the various sources for the desired genes are located and obtained, they are studied relative to the location of useful restriction sites. These are short DNA sequences that interact with specific restriction endonucleases that are readily available from multiple commercial sources. The selection of which restriction endonucleases to use is based on the presence of the corresponding restriction sites flanking the coding regions for each gene desired. Once the restriction endonucleases are selected, they are combined with the source DNA and incubated under conditions known for each enzyme (e.g. 37° C. for 30 minutes). This results in DNA fragments which can be identified by their relative lengths when analyzed by gel electrophoresis (all methods are contained in Sambrook and many other commonly available lab manuals and also in technical information from the enzyme vendors). The desired fragments are isolated and purified by known methods.

The desired fragments are then combined in order and exposed to a DNA ligase enzyme under conditions also detailed in Sambrook et al. This rejoins the formerly separate fragments into the sequence (e.g. incubation at 37° C. for 30 minutes or at 4° C. for an hour). Each restriction product has two ends on a linear fragment. It should also be noted that in the ligation step like ends bind to like ends only in this process. In other words, digestion of pNW63 results in a linear fragment with a 'green' end and a 'black' end which when combined with the PxylA+xylR fragments from *B. megaterium* (itself having a 'brown' end and a 'green' end) the two fragments are joined through their respective 'green' ends. Thus, after combining all of the various restriction fragments through their common ends that are fragments flanked by two 'black' ends. The order may be green/green, brown/brown, orange/orange leading to a long fragment with two black ends which can then be joined by established means to join black/black and thus forming a circular construct. Any sequence of joining steps involving like to like may result in the same final product.

Example 2

Figure 6:
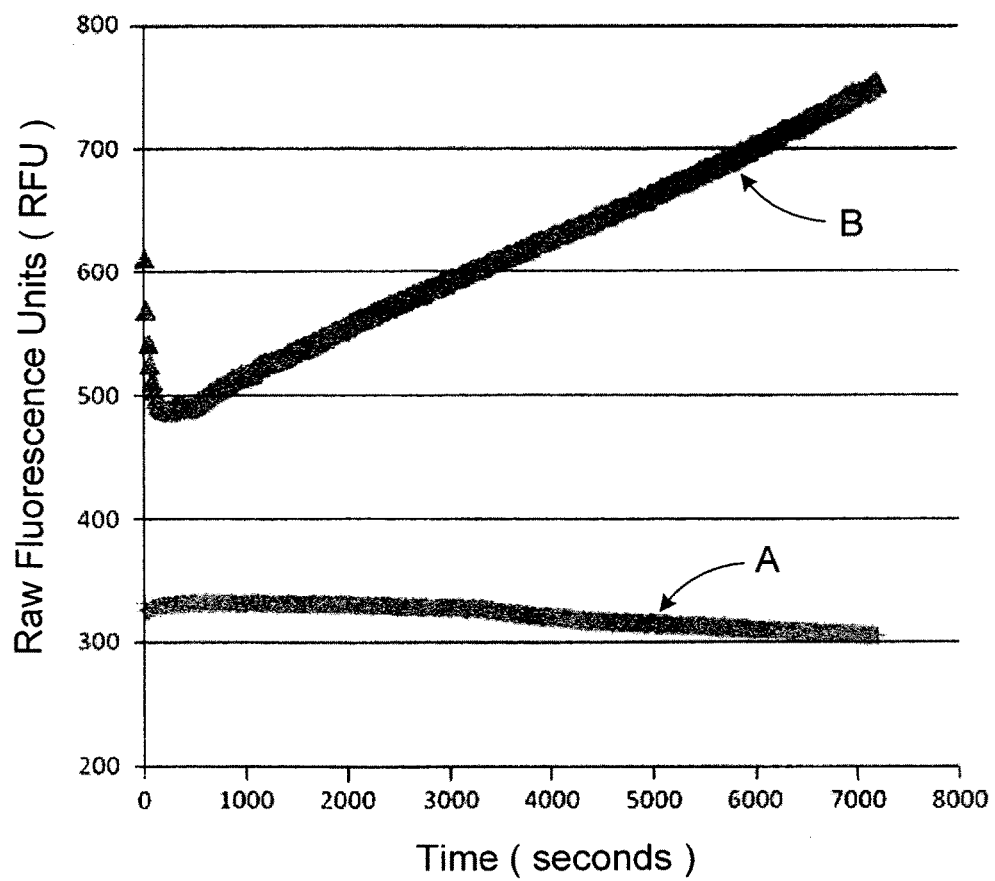
FIG. 6 is a graph showing the results of sterilization tests employing the inventive biological indicator.

A series of tests using a biological indicator (BI) in the form of *Geobacillus stearothermophilus* spores that contain the plasmid construct set out in SEQ ID No. 1 is conducted. Four unsterilized BIs (positive control) are run side-by-side with four BIs that are sterilized. The sterilized BIs are processed in a AMSCO SV120 steam autoclave using a standard gravity 121° C., 30 minute cycle. The Ms are placed in a recovery medium that contains an enzyme substrate, the enzyme substrate being 4-methylumbelliferyl-beta-D-galactopyranoside (MUG). The BIs are analyzed in a fluorescent incubator reader with the results being shown in FIG. 6. The curve labeled A is for the BIs that are sterilized, and the curve labeled B is for the BIs that are not sterilized. As indicated by the positive slope in curve B, active beta-galactosidase is constitutively and continuously produced which in the presence of the MUG produces a fluorescence. Only living spores can do this (proof of life).

The curve labeled A is from identical BI comprising the same materials but after having been exposed to the steam sterilization cycle. The flat line demonstrates that when the spores are killed, no beta-galactosidase is produced, and an increasing fluorescence is not observed over the same time interval (proof of death). The flat-line fluorescence which is seen is "native or back-ground" fluorescence seen in most materials but which does not increase over time.

While the disclosed invention has been explained in relation to specific embodiments, it is to be understood that various modifications thereof will become apparent to those skilled in the art upon reading the specification. Therefore, it is to be understood that the invention disclosed herein is intended to cover such modifications as may fall within the scope of the appended claims.

The invention claimed is:

1. A composition, comprising: a host organism comprising a spore forming bacteria selected from the group consisting of *Clostridium sporogenes, Clostridium difficle,* or *Clostridium botulinum;*
   a reporter gene for producing an indicator enzyme;
   a regulatory gene; and
   a vehicle for inserting the reporter gene and the regulatory gene in the host organism;
the host organism bearing a transposable genetic element in its genome for inserting an insertion sequence in the regulatory gene; the insertion sequence being selected from the group consisting of IS8402, ISH27-1, ISH27-2 and ISH 51-3, wherein the vehicle is taken up by the host organism, the insertion sequence is inserted in the regulatory gene, and the host organism undergoes sporulation.

2. The composition of claim 1, wherein the reporter gene comprises lacZ, bgaB, xylE, cat, gfp, or a mixture of two or more thereof.

3. The composition of claim 1, wherein the indicator enzyme comprises beta-D-galactosidase, beta-D-glucosidase, alpha-D-glucosidase, alkaline phosphatase, acid phosphatase, butyrate esterase, caprylate esterase lipase, chloroamphenicol acetyltransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, Page 3 of 7 alanine aminopeptidase, proline aminopeptidase, tyrosine aminopeptidase, phenylalanine aminopeptidase, beta-D-glucuronidase, fatty acid esterase, or a mixture of two or more thereof.

4. The composition of claim 1, wherein the reporter gene comprises bgaB, the reporter gene producing an indicator enzyme comprising beta-galactosidase.

5. The composition of claim 1, wherein the regulatory gene comprises xylR, lacI, tetR, or a mixture of two or more thereof.

6. The composition of claim 1, wherein the vehicle comprises a plasmid or a viral vector.

7. The composition of claim 6, wherein the plasmid comprises a circular double-stranded DNA.

8. The composition of claim 6, wherein the plasmid is linear.

9. The composition of claim 6, wherein the size of the plasmid is in the range from about 2000 to about 20000 base pairs.

10. The composition of claim 6, wherein from 1 to about 3000 copies of the plasmid are taken up by a cell of the test organism.

11. The composition of claim 6, wherein the plasmid comprises one or more origins of replication.

12. The composition of claim 6 wherein the plasmid comprises one or more genetic markers.

13. The composition of claim 6, wherein the plasmid comprises one or more multiple cloning sites.

14. The composition of claim 6, wherein the plasmid comprises one or more genes that provide a selective marker to induce the test organism to retain the plasmid.

15. The composition of claim 6, wherein the plasmid comprises a gram negative origin of replication and a gram positive origin of replication.

16. The composition of claim 15, wherein the gram negative origin of replication comprises *Escherichia coli*, and the gram positive origin or replication comprises *Geobacillus stearothermophilus, Bacillus atrophaeus*, or a mixture thereof.

17. The composition of claim 6, wherein the plasmid comprises an antibiotic resistance gene and/or a gene with exogenous nutritional capability.

18. The composition of claim 6, wherein the plasmid comprises a chloramphenicol, ampicillin or spectinomycin antibiotic gene, and/or a xylose, lactose or amino acid nutritional gene.

19. The composition of claim 6, wherein the viral vector comprises at least one gene transporter that comprises nucleic acid surrounded by a capsid.

20. The composition of claim 6 wherein the viral vector comprises at least one bacteriophage.

21. The composition of claim 6, wherein the viral vector comprises lambda or M13 bacteriophage.

22. The composition of claim 1, wherein the reporter gene comprises bgaB and the regulatory gene comprises xylR.

* * * * *

SEQUENCE LISTING

```
<160> NUMBER OF SEQ ID NOS: 1

<210> SEQ ID NO 1
<211> LENGTH: 11223
<212> TYPE: DNA
<213> ORGANISM: Artificial Sequence
<220> FEATURE:
<223> OTHER INFORMATION: Modified from Geobacillus stearothermophilus
<220> FEATURE:
<221> NAME/KEY: gene
<222> LOCATION: (1746)..(2059)
<223> OTHER INFORMATION: Xylose regulator
<220> FEATURE:
<221> NAME/KEY: misc_feature
<222> LOCATION: (2060)..(4166)
<223> OTHER INFORMATION: Transposable element
<220> FEATURE:
<221> NAME/KEY: gene
<222> LOCATION: (4167)..(5023)
<223> OTHER INFORMATION: Xylose regulator
<220> FEATURE:
<221> NAME/KEY: gene
<222> LOCATION: (6769)..(8016)
<223> OTHER INFORMATION: Mob/Pre protein
<220> FEATURE:
<221> NAME/KEY: gene
<222> LOCATION: (8245)..(9249)
<223> OTHER INFORMATION: Replication protein
<220> FEATURE:
<221> NAME/KEY: gene
<222> LOCATION: (9356)..(10006)
<223> OTHER INFORMATION: Chloramphenicol acetyl transferase
<220> FEATURE:
<221> NAME/KEY: gene
<222> LOCATION: (10401)..(1196)
<223> OTHER INFORMATION: Beta galactosidase

<400> SEQUENCE: 1
tcaaaaatga tcgcgacctc tgccttgatt ctagatccga ccaaacaatc taactttttc      60
agctcttgcc ctaactgtgt aacttcccta taaattctat tattctcgtt caaaaagtgg     120
ggcaccattg caccgtggaa tttttcagct cctgctctac tttgacgcca ctggaaaaac     180
ataataccat ctgcaccacg ggcaatagtt gcataactcc atagacgcat tacacctggc     240
ggttttggaa cattaatatc gcgccagtta acatgtgagg ttacctgctc catcaaaata     300
aacggttgac cttttcttaa actacgcata aggtcattca tcatggcgtg ctgaattggc     360
aagccctctc tgggatcagg atatgagtcc catgtcacaa tatctacatg ctgagcccat     420
tgaaaatagt ttaacggttt gaatgaaccc atgaaattag ttgatactgg aatatctggt     480
gttacctcac gtaaaatttc cttttctgtt aaaaacaact tgagaattga gtcattcata     540
aaacggtagt aatcaagttc ttgggatgga ttaataaaag ttggtgcctt tctaggggga     600
```

```
ttaatttcat cccaatgatt gtatcgctgt ccccaaaagt ttgtacccca acgttcattt      660
aattcatcga ttgttttata tctttccttt agccactttc taaacgcgac agcacaattc      720
tcacaaaaac acttggaaac gtgacatgca tactcattat taacatgcca cattttgagt      780
gccggatgat ttttataccg ttctgctata gccctcacaa gtctctttat gtgcgtaatt      840
aattgaggat gattaggaca ataatgttgt ctactgccaa acgagagaat gacaccgctt      900
tcatcgatcg gcaaagaatc tggatacttt tttacaaacc aagctggagt agttgcagtc      960
gccgtcccca agttaatata aacaccgtgg tcatatagta tatctataac cttgtctagc     1020
cattcaaagt cgaacactcc atcagacggt tcgatcttgc tccaactgaa aatccctaaa     1080
gatactaaat tcaccccgc tttttgcatc aacttagcat cttcatacca aatttcctct      1140
ggccattgct ctgggttata atctcctccg taacaaattg aggataacac attcataatt     1200
attcccccta gctaattttc gtttaattat aaattaagtt aaaatttagg tacctacgta     1260
ggatccccgg gaattctcat gtttgacagc ttatcatcgg caggccttag tggccagacg     1320
tcaggtggca cttttcgggg aaatgtgcgc ggaaccccta tttgtttatt tttctaaata     1380
cattcaaata tgtatccgct catgagacaa taaccctgat aaatgcttca ataatattga     1440 aaaggaaga gtgcggccgc ccgcgggagc tcggatccca tttcccccctt tgattttag      1500 atatcactag tctggaccat ttgtcatttc cccctttgat ttaagtgaac aagtttatcc     1560
atcaactatc ttaattgagt tagtttgttt atccaataaa ctaactttat ctcatcatat     1620
acaaaataaa tgtttatttc aatgtttttt ttagaaaatt tagttataat attagatatg     1680
atacttttaa atatctaatt caagcttcaa aaaacaccaa cttagttcgg tggataaaca     1740
aaggagtggt tattattcaa attgcagatc aagctttagt aaaaaaaatg aatcaaaaat     1800
taatattaga tgaaattttg aagaactccc ctgtctccag ggcaactctc tctgagatta     1860
caggattaaa caagtctact gtctcctctc aagtaaatac actgcttgaa aaagatttta     1920
tttttgaaat tggggcaggg caatctagag gcggcagaag acctgtaatg cttgttttta     1980
ataagaatgc aggctactcg attggtattg atataggagt cgactatctt aacggaattc     2040
taaccgactt agaaggaaat gtcaaggccg attatttttt ccccaaaatc gccggtttaa     2100
aattccccag aaggaccttt cattgatcct tctgtttttc ttcttggagc tctcttttccc    2160 gtaatcgata gctttccccc tttaggttga aaatgatgga atgatgcagt aatcgatcta     2220
acatcgctgt cgccaaaacc gagtctccca cgatttctcc ccattcccca aagcttttgt     2280
tggaggtgag gataatcggg gcatgctcgt accgccgggc gatcacttga ataagtaat     2340 gagcgctgtt cgggtccagt tttagatacc ccatttcatc aataatgaga acggttggct     2400
tcacaaagac acgaagcttt ttctccaact ttccttcctg gtcggctctt cttaactgat     2460
tgaccaaatc gtgagcggta ataaaatacg ttttatatcc tcttgcgatc gcctccattc     2520
caatcgaaat tgccagatgt gtcttcccaa tacccgtgg accagaaaag aggatatttt     2580
ctttccggtc aataaaggac aacgtaagca gttctcgaat ccggcgctca tccaccgaag     2640
gctgcgcggt aaaatcaaac gtatcgatcg tcttgcgata cggcagtttg gacagcttga     2700
tgagcgtttg gatcgatcgt gcctgttttt cgacgatttc tgcctctaat aagcggaata     2760
aaaactctga atatgatata ttatgagtag aggcgtattc tgccatggcg gaccatcgtt     2820
ccgccatgac aggcaaatgg agtcggtggc aatactcgtg tattcgttct ttcatgagct     2880
ttcccctcgc aggaatgcgt cataaacgga caatggacga gtatccactt ccaccgaaac     2940
```

```
aggcgaaatg gtggcggcca tttccgtttg tttcttttt atttttcgg cgaatgaaat    3000 cacttttttc tgttggtcca cgtgagaaat ctcctcccct cgaaagtaca atcgaatatc    3060
tccatttaat cgctccttca ccagaatttc tttgcccgca tactccgccg ataagagcca    3120
ttgttcccct ttgtaggaga aactgccatc ccaatgcacc ttccgatagg aaagatagct    3180
cgtatcgtaa tctttcaacg gaagaggctt gagtgactcc tcggcccaac gctcttgcgg    3240
agaaataccg gtagtggcgt ttggcttccg attcgccact tgatcgagcc aacgatggag    3300
aaggaaattt aattcctcga tgcttttcaaa cgctgtcccc acatagaagt gatccatgat    3360
atactgaatg gctcgttcga cttttcccctt tgtctgggcc cggtaaggcc ggcatacttt    3420
tggaataaat ccatagtaac tcgcaaattc ggaaaatcgt tgattccatt tcaccactcc    3480
ttgttctcgc ccgtctgtaa cggtcttcat attgtcaaat aacaccttct tcggaaccc    3540 gccaaagtac ttgaagctct gaatcaggca ttccattaag tgttcctgat cctggctggt    3600
cgtaaatacc gcgtatttca tccgcgaata gcctaacgtg gccacaaata gcgataactt    3660
gacttttttc cctttcgatca cgacctcccc aacttctttc caatcgactt gcatttgttc    3720
gccaggaagc gtttcataac gaacggtgta tttcttttc gccgtctctc ggaaaggttt    3780
catatagtct tttaaaatcg tctttcctcc cgtatagccc tgttgtcgaa tttcaaaaaa    3840
caacttttcg ctattaaaca ccccatcttc taacattcgt ttttgaagat acggcttaaa    3900
tggatctaac ttgctttttc tttgttttcg cttggatttg aaggaggat tgggggagtg    3960 aatatatttt cggacggttt tccgatcgat ccccaattcc ctcgcaatat cggaaatact    4020
cattcccctt tcatacatct ctttgatcat aaaaaattcc cctctcgtaa tcatgaacca    4080
tagctcctct cgttgacact atggttctat tgtaagtggg gaatttttatt ccggctatat    4140 tggggatttt atcatcggct ttaacagaaa tattattctc gagaagactt ctgacttgtc    4200
tagttcttcc gctagtgaag taaaagagat tttatttgca cttattcatg gttttgtaac    4260
ccatatgcct gagtccccctt atggtctagt cggaatagga atttgtgttc caggccttgt    4320
agatcgtcat cagcaaatta ttttcatgcc taacttaaat tggaatatca aagatttgca    4380 gttttttaatt gagagtgagt ttaatgttcc ggttttttgtt gaaaatgaag ctaatgcagg    4440
agcatacggt gaaaaagtat ttggtatgac aaaaaactat gaaaacatcg tttacatcag    4500
tattaatatc ggaattggaa ctggacttgt tattaacaac gaattgtata aggtgttca    4560 gggttttttct ggggaaatgg gtcatatgac gatagatttt aatggaccca aatgcagctg    4620
tggaaatcga ggctgttggg aattatatgc ttctgaaaaa gcgttactgg cttcgctctc    4680
taaagaagaa aagaatatttt ctcgaaaaga gattgtggaa cgcgcaaata aaaatgatgt    4740
agaaatgtta aatgcacttc aaaactttgg ctttttatatc ggaattggat taaccaatat    4800
ccttaataca tttgatatag aagctgttat cttgagaaat catataattg aatctcatcc    4860
cattgtttta aatacgatta aaaacgaagt ttccttctaga gtccattctc atttagacaa    4920
taaatgtgaa ctattgcctt cttcgttagg aaaaaatgca cctgctttag gagcggtttc    4980
tatcgttatt gattcttttt taagtgttac ccctataagt taggagctcc ccgggacgtt    5040
cttgccattg ctgcataaaa aacgcccggc ggcaaccgag cgttctgaat taattaatca    5100
tcgcgactgc agagatatcg atttcaagct atatttggag ttgagcctct tgaaacggac    5160
accctgtatc cgaaggatcg aaacgctgtc agggcctttg tggcccgact ctagaggatc    5220
cccgggtacc gagctcgaat tcaatttcac aatcagagag aacgggaaag taaaacgaat    5280
cccgatattg ataaagaacg gtcacatgaa aattatgatt tggtgaatga tgaaccgatc    5340
```

| | |
|---|---|
| gactataacg agcgagtaaa agaaattatt ggtaactgtc agaccaagtt tactcatata | 5400 |
| tactttagat tgatttaaaa cttcattttt aatttaaaag gatctaggtg aagatccttt | 5460 |
| ttgataatct catgaccaaa atcccttaac gtgagttttc gttccactga gcgtcagacc | 5520 |
| ccgtagaaaa gatcaaagga tcttcttgag atcctttttt tctgcgcgta atctgctgct | 5580 |
| tgcaaacaaa aaaaccaccg ctaccagcgg tggtttgttt gccggatcaa gagctaccaa | 5640 |
| ctcttttttcc gaaggtaact ggcttcagca gagcgcagat accaaatact gttcttctag | 5700 |
| tgtagccgta gttaggccac cacttcaaga actctgtagc accgcctaca tacctcgctc | 5760 |
| tgctaatcct gttaccagtg gctgctgcca gtggcgataa gtcgtgtctt accgggttgg | 5820 |
| actcaagacg atagttaccg gataaggcgc agcggtcggg ctgaacgggg ggttcgtgca | 5880 |
| cacagcccag cttggagcga acgacctaca ccgaactgag atacctacaa cgtgagctat | 5940 |
| gagaaagcgc cacgcttccc gaagggagaa aggcggacag gtatccggta agcggcaggg | 6000 |
| tcggaacagg agagcgcacg agggagcttc caggggggaaa cgcctggtat ctttatagtc | 6060 |
| ctgtcgggtt tcgccacctc tgacttgagc gtcgattttt gtgatgctcg tcagggggggc | 6120 |
| ggagcctatg gaaaaacgcc agcaacgcgg cctttttacg gttcctggcc ttttggttac | 6180 |
| cttgaatgta tataaacatt ctcaaaggga tttctaaatc gttaagggat caactttggg | 6240 |
| agagagttca aaattgatcc ttttttttata acaggaattc aaatcttttt gttccattaa | 6300 |
| agggcgcgat tgctgaataa aagatacgag agacctctct tgtatctttt ttattttgag | 6360 |
| tggttttgtc cgttcactaa gaaaccgaaa agacaataaa aatttattc ttgctgagtc | 6420 |
| tggctttcgg taagctagac aaaacggaca aaataaaaat tggcaagggt ttaaaggtgg | 6480 |
| agattttttg agtgatcttc tcaaaaaata ctacctgtcc cttgctgatt tttaaacgag | 6540 |
| cacgagagca aaaccccccct tgctgaggt ggcagagggc aggtttttt gtttcttttt | 6600 |
| tctcgtaaaa aaaagaaagg tcttaaaggt tttatggttt tggtcggcac tgccgacagc | 6660 |
| ctcgcagagc acacacttta tgaatataaa gtatagtgtg ctatacttta cttggaagtt | 6720 |
| gcgccgattt gtcatgacaa attttctcga aagcgaggtc gaaataaat gagttttgca | 6780 |
| gtagtccgta tgcagaaaat gaagtcccat gatctgaaag gaattcaatt tcacaatcag | 6840 |
| agagaacggg aaagtaaaac gaatcccgat attgataaag aacggtcaca tgaaaattat | 6900 |
| gatttggtga atgatgaacc gatcgactat aacgagcgag taaagaaat tattgaatca | 6960 |
| caaaaagttg ggacgagaaa aacaagaaaa gatgctgtgc ttgtaaatga attacttgtc | 7020 |
| acgtctgatc ggtattttt tgagcgatta gagcctgatg aacagaaacg atttttgag | 7080 |
| gaaagttata aattatttgc tgatcgatat gggaaacaaa atattgcgta tgcgactgtt | 7140 |
| cacatgacg agaaacccc tcacatgcat ttaggagttg ttcctatgcg cgatggaaaa | 7200 |
| ttgcaaggaa aaaatgtgtt taatcgtcaa gaattgttgt ggctgcaaga caagtttcca | 7260 |
| gagcatatgc agaagctcgg ttttgattta caacgtggaa aaaaggttc ggatcgagag | 7320 |
| catattgaaa tgagtaaatt taaaaaacaa acgttagaaa aagagattga tcttttagag | 7380 |
| aatgaattga aaataaaaa aagtgagttg gcgattctat ctgaagaagt ttcaggcgaa | 7440 |
| tttaagattc cagtgaaaag agaaagaaa agtgttgaag ttccaacagg gaaacgaaat | 7500 |
| cttttgggga tcgagcaaaa gaaaacggtt atgaaatcaa cggggaatgt aattttaaaa | 7560 |
| gacgaagtgt tcaagatttt gaagaaaaaa gtaaaagcag gcgcacttt gcaaacgaga | 7620 |
| gtggatcagt tgttaaatac tgatttcgca aaagagaatc aatcgctgaa aatgaagtg | 7680 |

```
aaagagttgc gatctacaaa taaatcttta tccgaagaaa atggtcgttt aaagagcgca   7740
gtagagcatt taacgaatga gatcgaaagt ttatatgtat tgacgaaaga tttcttaaaa   7800
gcccgtacaa gcgatttaga gagctttaag gagttgtttg gggtatttgt aggtaaagtg   7860
aaagaaaaag cgcctagagg gcttttcgtg cgtcagcatg agcgatcgga agaaaagaag   7920 aatactttt  cgcttcaaga tgttttgcag cgtgatcgag aacttcgtga gcaaagaaaa   7980
gcaaagagga aaaaatcgca tgatttggag cgataagaaa aagcactcga atgagtgctt   8040
tttttgcgtt ttgagcgtag cgaaaaacga gttctttcta ttcttgatac atatagaaat   8100
aacgtcattt ttattttagt tgctgaaagg tgcgttgaag tgttggtatg tatgtgtttt   8160
aaagtattga aaacccttaa aattggttgc acagaaaaac cccatctgtt aaagttataa   8220
gtgaccaaac aaataactaa atagatgggg gtttctttta atattatgtg tcctaatagt   8280
agcatttatt cagatgaaaa atcaagggtt ttagtggaca agacaaaaag tggaaaagtg   8340
agaccatgga gagaaaagaa aatcgctaat gttgattact ttgaacttct gcatattctt   8400
gaatttaaaa aggctgaaag agtaaaagat tgtgctgaaa tattagagta taaacaaaat   8460
cgtgaaacag gcgaaagaaa gttgtatcga gtgtggtttt gtaaatccag gctttgtcca   8520
atgtgcaact ggaggagagc aatgaaacat ggcattcagt cacaaaaggt tgttgctgaa   8580
gttattaaac aaaagccaac agttcgttgg ttgtttctca cattaacagt taaaaatgtt   8640
tatgatggcg aagaattaaa taagagtttg tcagatatgg ctcaaggatt tcgccgaatg   8700
atgcaatata aaaaaattaa taaaaatctt gttggtttta tgcgtgcaac ggaagtgaca   8760
ataaataata aagataattc ttataatcag cacatgcatg tattggtatg tgtggaacca   8820
acttatttta agaatacaga aaactacgtg aatcaaaaac aatggattca attttggaaa   8880
aaggcaatga aattagacta tgatccaaat gtaaagttc  aaatgattcg accgaaaaat   8940
aaatataaat cggatataca atcggcaatt gacgaaactg caaaatatcc tgtaaaggat   9000
acggatttta tgaccgatga tgaagaaaag aatttgaaac gtttgtctga tttggaggaa   9060
ggtttacacc gtaaaaggtt aatctcctat ggtggtttgt taaaagaaat acataaaaaa   9120
ttaaaccttg atgacacaga agaaggcgat ttgattcata cagatgatga cgaaaaagcc   9180
gatgaagatg gattttctat tattgcaatg tggaattggg aacggaaaaa ttatttttatt  9240 aaagagtagt tcaacaaacg ggattgactt ttaaaaaagg attgattcta atgaagaaag   9300
cagacaagta agcctcctaa attcacttta gataaaaatt taggaggcat atcaaatgaa   9360
ctttaataaa attgatttag acaattggaa gagaaaagag atatttaatc attatttgaa   9420
ccaacaaacg acttttagta taaccacaga aattgatatt agtgttttat accgaaacat   9480
aaaacaagaa ggatataaat tttaccctgc atttattttc ttagtgacaa gggtgataaa   9540
ctcaaataca gcttttagaa ctggttacaa tagcgacgga gagttaggtt attgggataa   9600
gttagagcca ctttatacaa ttttttgatgg tgtatctaaa acattctctg gtatttggac   9660
tcctgtaaag aatgacttca aagagtttta tgatttatac ctttctgatg tagagaaata   9720
taatggttcg gggaaattgt ttcccaaaac acctatacct gaaaatgctt tttctctttc   9780
tattattcca tggacttcat ttactgggtt taacttaaat atcaataata atagtaatta   9840
ccttctaccc attattacag caggaaaatt cattaataaa ggtaattcaa tatatttacc   9900
gctatcttta caggtacatc attctgtttg tgatggttat catgcaggat tgtttatgaa   9960
ctctattcag gaattgtcag ataggcctaa tgactggctt ttataatatg agataatgcc  10020
gactgtactt tttacagtcg gttttctaat gtcactaggg ctcgcctttg ggaagtttga  10080
```

```
agggctggca cgacaggttt cccgactggc ctcattggcc tagatatgac gacaggaaga    10140
gtttgtagaa acgcaaaaag gccatccgtc aggatggcct tctgcttaat ttgatgcctg    10200
gcagtttatg gcgggcgtcc tgcccgccac cctccgggcc gttgcttcgc aacgttcaaa    10260
tccgctcccg gcggatttgt cctactcagg agagcgttca ccgacaaaca acagataaaa    10320
cgaaaagccc agtctttcga ctgagccttt cgttttattt gatgggccta gttggcccca    10380
actgtcggaa cgagacttct ctaaaccttc ccggcttcat catgctctct taacactgct    10440
acatcaaccc cttgaatcct caattcacct cctcgaaaac atttcccatc aatcatattc    10500
tggtatatct tatcttctgg cagtgacagc gtcacttcgt aatcattatg attgatgata    10560
atcaaatact tccattcatc agtctctctt tgttgcacct ctacattttc agctacttca    10620
agaatgggat taatatgatg tttagcgaaa acctgttcta aaagcctgcc taaataatta    10680
ctatctggat aagtaccgac gtaaatcccc tctcctttac cgtagcagtt acgtgtaacc    10740
gccggaagtc ctgcatacca atcccccctta aatgtcgcta gaggttctgc cccttctaat    10800
cggattatgt ccgcccacgt cgtacaatca tattccccat cgttactata tattttgttt    10860
acctttattt ctgggtatgg tacaaattca tcaacaaaaa tccccaaaat atctcgcaga    10920
ggaccaggat atccgcctag atgtacacgg tcattttcat ctacaatgcc actgaagaaa    10980
ctgacaatca aagtgccacc gttagcaaca aattgccgta agttttcatc ttctccctct    11040
ttaaccatat ataacattgg agcaataact actttgtatt ttgttagatc atcagatggc    11100
cttacaaaat cgacagcaat attacgttta tataattccc tataataagc ttcaactata    11160
ggaatatatc ttagtttatt atgtggtttg gaacttagtt cgacagccca ccagttttcc    11220
caa                                                                  11223
```